(12) United States Patent
Qu et al.

(10) Patent No.: US 8,294,898 B2
(45) Date of Patent: Oct. 23, 2012

(54) ROTATIONALLY ASYMMETRIC CHAOTIC OPTICAL MULTI-PASS CAVITY

(75) Inventors: Dongxia Qu, Princeton, NJ (US); Claire Gmachl, Princeton, NJ (US)

(73) Assignee: Trustees of Princeton University, Princeton, NJ (US)

( * ) Notice: Subject to any disclaimer, the term of this patent is extended or adjusted under 35 U.S.C. 154(b) by 906 days.

(21) Appl. No.: 12/197,558

(22) Filed: Aug. 25, 2008

(65) Prior Publication Data

US 2009/0059235 A1 Mar. 5, 2009

Related U.S. Application Data

(60) Provisional application No. 60/968,450, filed on Aug. 28, 2007.

(51) Int. Cl.
*G01N 21/00* (2006.01)
*H01S 3/08* (2006.01)
(52) U.S. Cl. ........... 356/437; 356/236; 356/626; 372/99
(58) Field of Classification Search .......... 356/432–437, 356/233–236, 246, 440, 626; 372/99, 92, 372/107
See application file for complete search history.

(56) References Cited

U.S. PATENT DOCUMENTS

| | | | | |
|---|---|---|---|---|
| 3,920,336 A * | 11/1975 | Sackett | ........................... | 356/440 |
| 3,977,787 A * | 8/1976 | Fletcher et al. | ............... | 356/451 |
| 4,575,252 A * | 3/1986 | Akiyama | ....................... | 356/446 |
| 4,677,112 A * | 6/1987 | Butler et al. | .................... | 514/312 |
| 4,934,816 A * | 6/1990 | Silver et al. | .................... | 356/409 |
| 5,068,739 A * | 11/1991 | Filo | ................................. | 348/96 |
| 5,241,459 A * | 8/1993 | Kaplan et al. | .................. | 362/298 |
| 5,258,363 A * | 11/1993 | Hed | ................................. | 505/160 |
| 5,268,732 A * | 12/1993 | Sato | ............................... | 356/73.1 |
| 5,363,232 A * | 11/1994 | Tokue | ............................ | 359/234 |
| 5,818,578 A * | 10/1998 | Inman et al. | ................... | 356/246 |
| 6,147,350 A * | 11/2000 | Beecroft et al. | .......... | 250/339.08 |
| 6,844,553 B2 * | 1/2005 | Daly et al. | ................ | 250/339.07 |
| 6,846,085 B2 * | 1/2005 | Minneman et al. | ........... | 359/838 |
| 7,215,428 B2 * | 5/2007 | McNeal et al. | ................ | 356/440 |
| 7,236,252 B1 * | 6/2007 | Carreiro et al. | ............... | 356/498 |
| 7,307,716 B2 * | 12/2007 | Silver | ............................ | 356/246 |
| 7,535,559 B2 * | 5/2009 | Yoshimura | ..................... | 356/236 |
| 7,586,114 B2 * | 9/2009 | Cole et al. | ...................... | 250/575 |

(Continued)

OTHER PUBLICATIONS

Narimanov, E., et al., "Compact Quasi-Chaotic Optical Cavity", 2005 Quantum Electronics and Laser Science Conference (QELS).

(Continued)

*Primary Examiner* — Sang Nguyen
(74) *Attorney, Agent, or Firm* — Niels Haun; Dann, Dorfman, Herrell & Skillman, P.C.

(57) ABSTRACT

The present invention relates to a rotationally asymmetric chaotic optical multi-pass cavity useful in optical gas sensing spectroscopy, optical delay lines, and laser amplification systems, for example. The cavity may include a single closed mirror having a light reflective surface that is deformed in two orthogonal directions and more particularly, but not exclusively, in the shape of a quadrupole in both horizontal and vertical planes. The cavity includes a light entry port and a light exit port which may be the same or separate ports, as well as a gas inlet and a gas outlet. The optical path length, the beam divergence rate, and the spot pattern are controlled by selecting the cavity deformation coefficients and the input beam direction to achieve the desired beam path and beam quality.

9 Claims, 22 Drawing Sheets

U.S. PATENT DOCUMENTS

| | | | | |
|---|---|---|---|---|
| 7,595,875 | B1* | 9/2009 | Mitchell | 356/328 |
| 7,656,532 | B2* | 2/2010 | Cole | 356/432 |
| 7,663,756 | B2* | 2/2010 | Cole | 356/437 |
| 8,018,981 | B2* | 9/2011 | Eckles et al. | 372/99 |

OTHER PUBLICATIONS

Qu, D., et al., "Modeling and Design of a Highly Compact Chaotic Cavity for Optical Gas Sensing Applications", IEEE Sensors 2007 Conference, Oct. 2007.

McManus, J.B., et al., "Astigmatic Mirror Multipass Absorption Cells for Long-Path-Length Spectroscopy", Applied Optics, vol. 34, No. 18, Jun. 20, 1995.

Nockel, J., et al., "Chaotic Light: A Theory of Asymmetric Resonant Cavities", Optical Processes in Microcavities, World Scientific Publishers, 1996.

Colombelli, R., et al., "Surface-Plasmon Quantum Cascade Microlasers With Highly Deformed Resonators", IEEE Journal of Selected Topics in Quantum Electronics, vol. 12, No. 1, Jan./Feb. 2006.

Lacey, S., et al., "Directional Emission from Whispering-Gallery Modes in Deformed Fused-Silica Micropheres", Dec. 15, 2001, vol. 26, No. 24, Optics Letters.

Schwefel, H., et al., "Dramatic Shape Sensitivity of Directional Emission Patterns From Similarly Deformed Cylindrical Polymer Lasers", vol. 21, No. 5, May 2004, J. Opt. Soc. Am. B.

Hao, L., et al., "Cylindrical Mirror Multipass Lissajous System for Laser Photoacoustic Spectroscopy", Review of Scientific Instruments, vol. 73, No. 5, May 2002.

Arkhipov, R., et al., "Compact Optical Delay Line for Investigations of Fast Processes", Sov. J. Quan. Electro., vol. 6, No. 5, May 1976.

Dingjan, J., et al., "Experimental Observation of Wave Chaos in a Conventional Optical Resonator", Physical Review Letters, vol. 88, No. 6, Feb. 11, 2002.

Li, M., et al., "Flexible Aberration-Free Multipass Amplifier and Compressor for Ultrashort-pulse Amplification", J. Opt. Soc. Am. B., vol. 15, No. 9, Sep. 1998.

Herriott, D., et al., "Folded Optical Delay Lines", Aug. 1965, vol. 4, No. 8, Applied Optics.

Gmachl, et al., "High-Power Directional Emission from Microlasers with Chaotic Resonators", Science 280, 1556 (1998).

Hsiung, P., et al., "High Speed Path-Length Scanning With a Multiple-Pass Cavity Delay Line", Applied Optics, vol. 42, No. 4, Feb. 1, 2003.

White, J., "Long Optical Paths of Large Aperture", J.O.S.A., vol. 32, May 1942.

Herriott, D., et al., "Off-Axis Paths in Spherical Mirror Interferometers", Apr. 1964, vol. 3, No. 4, Applied Optics.

Chernin, S., et al., "Optical Multipass Matrix Systems", Jan. 1, 1991, vol. 30, No. 1, Applied Optics.

Nockel, J., et al., "Ray and Wave Chaos in Asymmetric Resonant Optical Cavities", Nature 385, 45 (1997).

Mekis, A., et al., "Ray Chaos and Q Spoiling in Lasing Droplets", vol. 75, No. 14, Physical Review Letters, Oct. 2, 1995.

Narimanov, E., et al., "Semiclassical Theory of the Emission Properties of Wave-Chaotic Resonant Cavities", vol. 83, No. 24, Physical Review Letters, Dec. 13, 1999.

White, J., "Very Long Optical Paths in Air", J. Opt. Soc. Am, vol. 66, No. 5, May 1976.

Silver, J., "Simple Dense-Pattern Optical Multipass Cells", Nov. 1, 2005, vol. 44, No. 31, Applied Optics.

Aben, H., et al., Interference Blots and Fringe Dislocations in Optics of Twisted Birefringent Media, J. Opt. Soc. Am. A,. vol. 15, No. 9, Sep. 1998.

Antonsen, E., et al., "Herriott Cell Interferometry for Millimeter-Scale Plasma Measurements", Review of Scientific Instruments, vol. 74, No. 3, Mar. 2003.

Krasnoperov., L., et al., "High-Temperature Shock Tube Studies Using Multipass Absorption: Rate Constant Results for OH + CH, OH + CH, and the Dissociation of CHOH" J. Phys. Chem A, 2004, 108 (40).

McManus, J., et al., "Atmospheric Methane Measurement Instrument Using a Zeeman-Split He-Ne Laser", Applied Optics, vol. 28, No. 23, Dec. 1, 1989.

Roller, C., "Carbonyl Sulfide Detection with a Thermoelectrically Cooled Mininfrared Quantum Cascade Laser", Optics Letters, vol. 28, No. 21, Nov. 1, 2003.

Yangagawa, T., et al., "CH4 Monitoring in Ambient Air by Communication Band Laser Diode Based Difference Frequency Generation in a QuasiPhase-Matched LiNbO3 Waveguide", Applied Physics Letters 89, 221115, 2006.

Nelson, D., et al., "Characterization of a Near-Room-Temperature, Continuous-Wave Quantum Cascade Laser for Long-Term, Unattended Monitoring of Nitric Oxide in the Atmosphere", Optics Letters, vol. 31, No. 13, Jul. 1, 2006.

Antonsen, E., "Fast Surface Temperature Measurement of Teflon Propellant-In-Pulsed Ablative Discharges Using HgCdTe Photovoltaic Cells", Review of Scientific Instruments 77, 103107, 2006.

Roscoe, H., et al., "Measurement Techniques in Gas-Phase Tropospheric Chemistry: A Selective View of the Past, Present, and Future", Science 276, 1065, 1997.

Miklos, A., et al., "Multipass Acoustically Open Photoacoustic Detector for Trace Gas Measurements", Apr. 10, 2006, vol. 45, No. 11, Applied Optics.

Horberger, Ch., et al., Sensitive Photoacoustic Overtone Spectroscopy of Acetylene with a Multipass Photoacoustic Cell and a Colour Centre Laser at 1.5 um, Chemical Physics 190, 1995, pp. 171-177.

Krasnoperov, L., et al. "Shock Tube Studies Using a Novel Multipass Absorption Cell: Rate Constant Results for OH + H and OH + CH", The Journal of Physical Chemistry, 2004, 108 (26).

* cited by examiner

US 8,294,898 B2

ROTATIONALLY ASYMMETRIC CHAOTIC OPTICAL MULTI-PASS CAVITY

RELATED APPLICATIONS

This application claims the benefit of priority of U.S. Provisional Application No. 60/968,450, filed on Aug. 28, 2007, the entire contents of which application is incorporated herein by reference.

GOVERNMENT LICENSE RIGHTS

This invention was made with government support under MIRTHE-EEC-0540832 awarded by the National Science Foundation. The government has certain rights in the invention.

FIELD OF THE INVENTION

The present invention relates generally to a rotationally asymmetric chaotic optical multi-pass cavity, and more particularly, but not exclusively, to a single closed reflecting surface having the shape of a quadrupole, and to the use of such cavities in optical gas sensing.

BACKGROUND

A multi-pass cavity or cell is an optical device, in which light bounces between mirrors a number of times in at least one stable orbit before exiting the system. A traditional multi-pass cell has a fairly complex structure that typically includes a glass tube, two large aperture mirrors, two end assemblies, and one base plate. Two concave, highly reflective mirrors are mounted on the end assemblies, through which one can adjust the distance between the mirrors. Inside the cell, a laser beam undergoes multiple reflections between the mirrors and traces out dense patterns at the mirror surfaces. The path length, and likewise the beam pattern, can be adjusted by changing the distance between the two mirrors. This design principle was first introduced in 1942. Since then, a variety of multi-pass cells have been developed such as Herriott cells, modified White cells, and improved Herriott cells, but the cell architecture and basic design strategy, based on integrable dynamics under the condition of paraxial ray approximations, remain almost the same. In contrast, non-integrable systems support more variable and complex dynamics with chaos, mixed-mode resonances, or scar modes. Some chaotic non-integrable cavities, such as deformed cylinders and deformed spheres, have been used as laser cavities, multi-pass optical cavities, and cavity ring-down resonators. Nevertheless, previous experimental and theoretical studies have mostly focused on cavities that retain some axial symmetry.

A highly compact Herriott cell can achieve an 11.7 m path length in a cell volume of 42 $cm^3$, and a recently-developed cylindrical mirror multi-pass cell can realize a 174-pass orbit with a mirror separation of only 7.32 cm. However, these systems have two limitations. First, when the cavity is further miniaturized so that the mirror radius is comparable with the size of the spot pattern, the paraxial ray approximation becomes insufficient, as the approximation cannot precisely predict the ray dynamics any more. Second, the alignment of the conventional multi-pass systems is nontrivial: 1) due to the multiple focusing components, and 2) the un-avoidable adjustment of the intermirror spacing. Because these systems require regular intermirror alignment, they are not suitable for unattended field deployment.

One application of interest for the multi-pass cell is as a gas sensor. In a gas sensor, the gas sample is contained in the multi-pass cell and a laser beam is directed through the gas which absorbs laser light at specified wavelengths. The type of molecular species in the cell is identified by observing the wavelength of the energy absorbed. Since the sensitivity of an absorption experiment generally increases with the optical path length and since the measurement response time correlates with the volume of a multi-pass cell, the capability of achieving a long optical path in a small cell volume is especially desired in laser absorption spectroscopy. That is, to accomplish a substantial absorption, a long optical path is generally required. A multi-pass cell is therefore an often used component for gas sensing systems; its optical path length determines the sensitivity and the cell volume critically affects the response time.

In the context of gas sensing, existing multi-pass cells have several drawbacks. First, a typical cell is around 1000 $cm^3$ in volume, which lengthens the cell response time corresponding to the time needed to replace the gas in the cell. Second, high precision in mirror manufacturing is required, which makes systems rather expensive. Third, vibrations or misalignments of the mirrors deteriorate the accuracy of spectrometric measurements. A complicated mirror alignment process and need for maintenance is a particular requirement in gas sensing applications. Therefore, traditional multi-pass cells are not suitable for low cost, compact, and portable gas sensing applications.

Recently, a design strategy was proposed to overcome the limitations of paraxial approximations and intermirror alignments in conventional multi-pass cells by taking advantage of quasi-chaotic ray dynamics in a single closed-surface cavity. (E. Narimanov, J. A. Fan, and C. Gmachl, Tech. Digest. Quantum Electronics and Laser Science Conference (QELS) 1, 421 (2005).) Such a chaotic cavity generally shows a mixture of stable, quasi-chaotic, and chaotic regions in the corresponding phase space. Any ray trajectories, once injected into the stable or quasi-chaotic regions, can be confined within the same region for a long time, whether they obey the paraxial approximation or not. Similar behavior has been studied in deformed dielectric spheres and microcylindrical chaotic cavities. Since quasi-chaotic ray trajectories are sensitive to their initial conditions, varying the initial conditions of the input beam can produce various ray trajectories. Furthermore, the quasi-chaotic multi-pass cell is easier to align and fabricate. Compared with the White cell and Herriott cell, which consist of at least two separate mirrors, the chaotic multi-pass cell has only one mirror. The single mirror enables straightforward alignment due to the closed structure that makes the intermirror alignment unnecessary. Moreover, the closed cavity structure favors manufacture by using either traditional (molding and milling) or advanced (stereolithography) fabrication techniques.

The challenge in designing quasi-chaotic multi-pass cells is to control the tendency of the chaotic beam to diverge. The initial design presented in Narimanov is a one-dimensionally deformed quadrupole sphere, defined as $R=R_0(1+\epsilon \cos 2\theta)$ in the standard spherical coordinates $(R, \phi, \theta)$, where $R_0$ is the average radius and $\epsilon$ is the deformation parameter. This cavity is featured with a rotationally symmetric structure in the $\phi$ direction. However, the beam size of the optical orbit in such a cavity grows linearly in the $\theta$-direction due to the axial symmetry of the device, which leads to uncontrolled chaos in the symmetric direction.

In view of the above, it would be an advance in the state of the art of multi-pass cells and optical gas sensing to develop multi-pass cells which are compact in size, are less susceptible to vibrations and mirror misalignment, and do not suffer from uncontrolled chaos.

SUMMARY OF THE INVENTION

The present invention relates to a rotationally asymmetric chaotic cavity that consists of a single closed reflecting surface. The cavity is based on quasi-chaotic ray dynamics in a 3-dimensional (3-D) deformed sphere. Within a small volume cavity, light can trace out a long optical path length with little beam overlap. The present invention has a simple structure and high mechanical/temperature stability, thus greatly facilitating the manufacturing process and yielding considerable cost savings. Compared to existing multi-pass cells, the chaotic multi-pass cell of the present invention has a much simpler, more compact, and more robust structure, and the manufacturing cost of such a cell is greatly reduced due to the compact structure. Therefore, systems of the present invention are suitable for low cost, compact, and portable gas sensing applications. An immediate application of the invention is for trace gas detection. Additional applications of the invention include optical amplifiers and optical delay lines.

Devices in accordance with a present invention comprise a number of useful features and advantageous performance characteristics. For example, the 3-D cavity is composed of a single closed reflecting surface rather than several separate reflecting mirrors currently used in multi-pass cells, and has no rotational symmetry. The cavity of the present invention can support chaotic or quasi-chaotic ray dynamics, and, in the phase space, the reflection points of the trajectory are confined inside some specific regions within hundreds of spatially separated reflections. In addition, the highly compact rigid cell structure is invulnerable to relative movement of the cavity shells and insensitive to temperature variations. Furthermore, the rotationally unsymmetrical cavity surface can self-focus the circulating beam with a global focus point, making the beam size small even after hundreds of reflections, so the light beam can exit the cavity through an optical port, which may also serve as the input hole. For the cavity of the present invention, the beam spots may spread out on the cavity surfaces, with sufficient space between the nearest spots and the optical port, to reduce beam overlap on the cavity surfaces in order to decrease the interference fringes. Still further, the cell volume for cavities of the present invention may be one magnitude smaller than current art devices. Due to the small volume, the cell can respond promptly to gas flows, thus greatly facilitating real-time gas measurement. Still further, the cell can support meter-scale optical path lengths with a centimeter size cavity diameter. It has been calculated that the cell can achieve at least a 16-meter optical path length with a mean cell radius of 2.54 cm.

Exemplary cells of the present invention are also easy to align without adjusting the relative distances between the two cavity shells and easy to manufacture due to the simple structure. The cell may be made of metal, alloy, plastic or other materials using standard milling technologies, yielding considerable cost savings. In addition, different incidence angles can lead to different path lengths even for the same cavity, which is useful, as different sensing applications may require different path lengths. Moreover, the cell design is very flexible, where, by changing the deformation parameters or the aspherical shapes, the cavity can achieve different multi-pass properties according to the requirements of the specific applications.

The chaotic multi-pass cavity may be realized by milling the interior cavity surface from a metal or plastic substrate using a standard milling system. Two identical half-cavity-shells may be manufactured, polished, coated, and assembled to form a multi-pass cavity. An optical port may be drilled and two gas ports may be put in the cavity shell. However, other acceptable methods, such as industry recognized fabrication techniques, such as molding, diamond turning, etc., may also be employed. Input light should be focused into the cavity with a wave front matched to the cavity radius. However, this limitation may be overcome by coupling light into the cavity with a lens.

Thus, in one of its aspects, the present invention provides a rotationally asymmetric chaotic optical multi-pass cavity, comprising a single closed reflecting that is deformed in two orthogonal directions and includes an optical inlet port through which light may be coupled into the cavity. For example, the reflecting surface of the rotationally asymmetric cavity may have the shape of a quadrupole in the x-y and the y-z planes. In addition, in another of its aspects, the present invention provides a system for optical gas sensing, comprising a rotationally asymmetric chaotic optical multi-pass cavity of the present invention. The gas sensing system may also include a source of electromagnetic radiation, such as a wavelength tunable laser, oriented to deliver electromagnetic radiation to the multi-pass cavity through the optical inlet port, and may also include a detector for receiving electromagnetic radiation emitted from the rotationally asymmetric chaotic optical multi-pass cavity. In yet a further aspect, the present invention provides a method for optical gas sensing, comprising providing a rotationally asymmetric chaotic optical multi-pass cavity in accordance with the present invention and introducing a gas to be tested into the cavity. The cavity may then be illuminated with a beam of incident electromagnetic radiation through the optical inlet port, and the radiation emitted from the cavity may be detected and analyzed to determine the nature of the gas to be tested. For instance, the step of illuminating the cavity may include illuminating the cavity over a plurality of wavelengths with a tunable laser, and step of analyzing the radiation may include determining the absorption of the incident electromagnetic radiation by the gas as a function of wavelength.

BRIEF DESCRIPTION OF THE DRAWINGS

The foregoing summary and the following detailed description of the preferred embodiments of the present invention will be best understood when read in conjunction with the appended drawings, in which.

DETAILED DESCRIPTION OF THE INVENTION

Figure 1A:
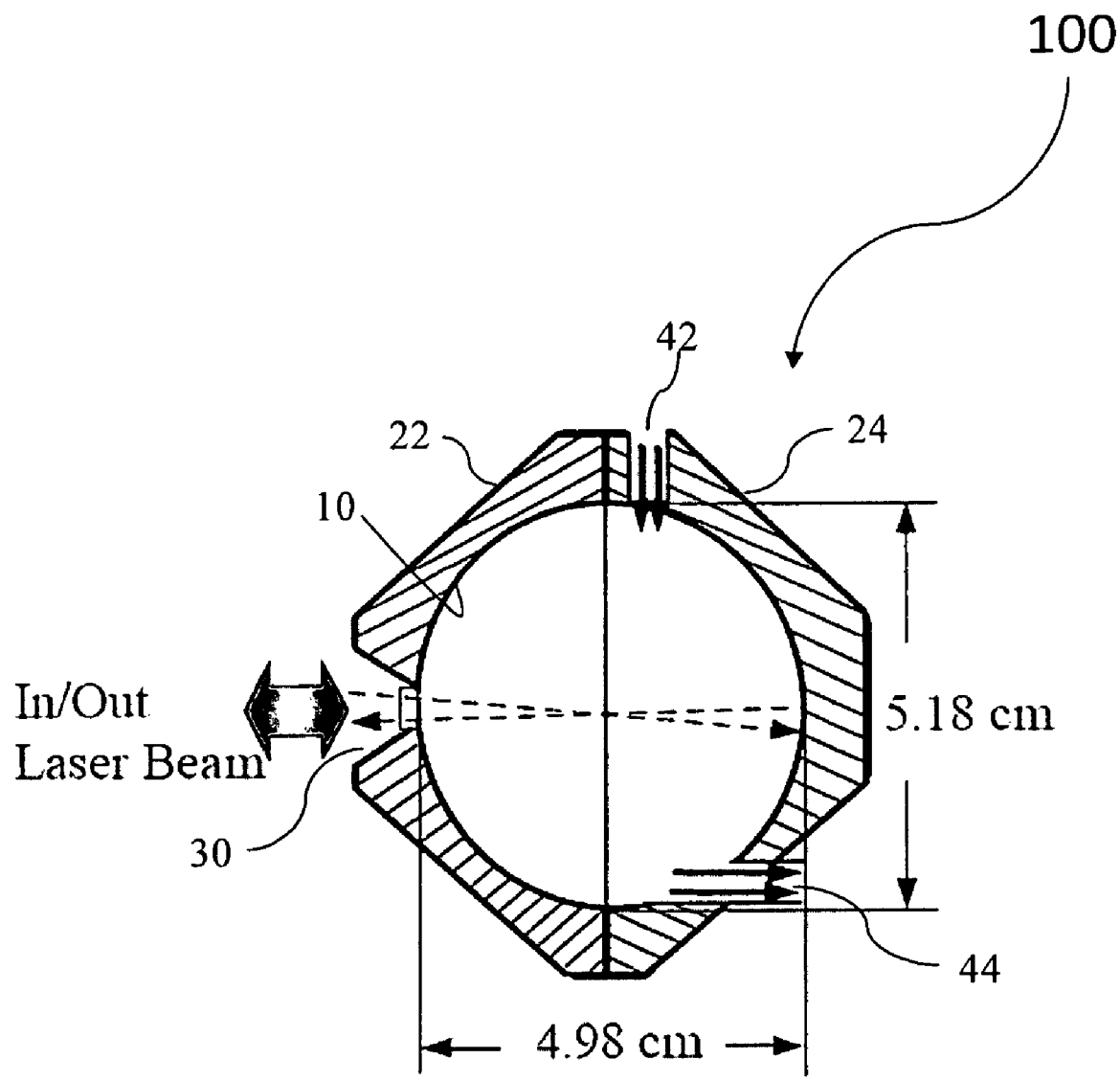
FIG. 1(a) schematically illustrates a cross-sectional view of a chaotic multi-pass cavity in accordance with the present invention.

Referring now to the figures, wherein like elements are numbered alike throughout, the present invention provides a multi-pass chaotic cavity, generally designated 100, FIG. 1(a). The cavity 100 is composed of a single, closed, reflecting cavity surface 10 formed by two asymmetric-shaped half-shells 22, 24 that are securely attached to each other. A small hole is provided as the optical port 30 to allow light to be coupled into and out-of the cavity 100. Inlet and outlet gas ports 42, 44 are located in regions of the surface 10 that do not interfere with the circulating rays and the optical port 30, so that rays exit the cavity 100 only after undergoing many reflections.

Figure 1B:
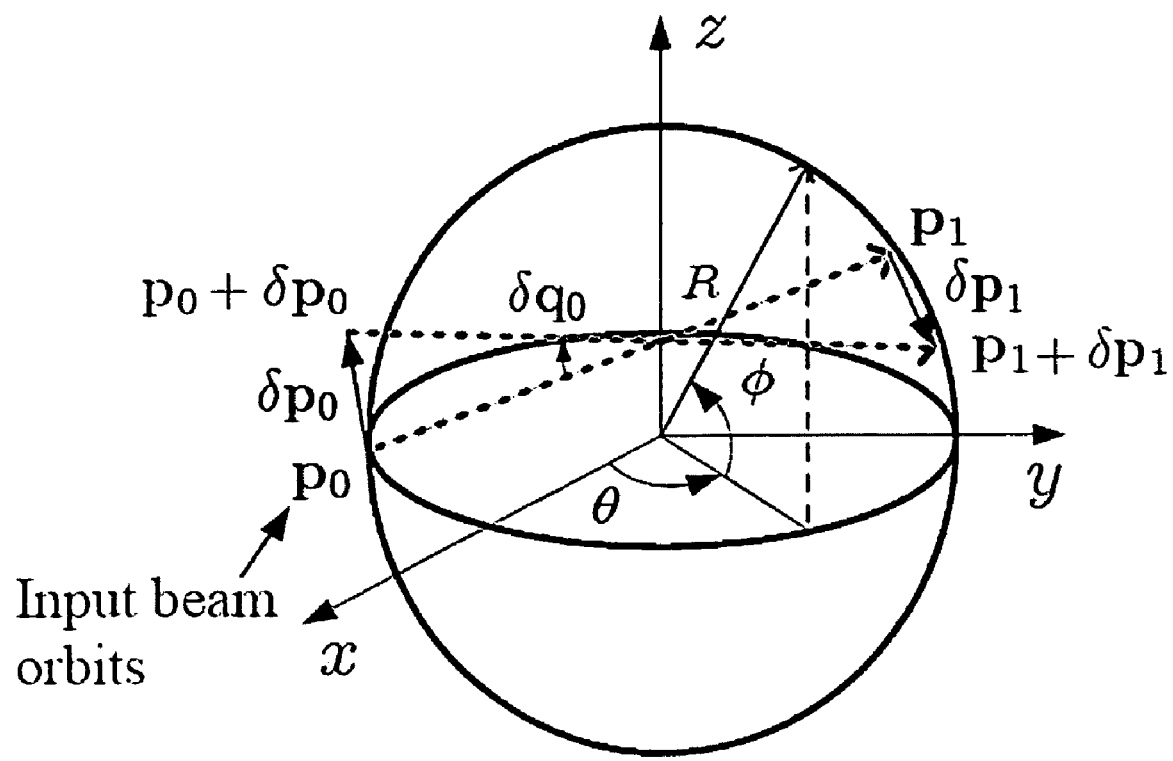
FIG. 1(b) schematically illustrates the three-dimensional (3-D) geometry of a chaotic multi-pass cavity in accordance with the present invention.

The 3-D chaotic cavity 100 has the shape of a quadrupole in the x-y and y-z planes. As shown in FIG. 1(b), the surface (x, y, z) can be specified by the spherical coordinates (R, θ, φ) as $$x = \frac{R_0[1 + \epsilon_{yz}\cos(2\varphi')]\sin\varphi'[1 + \epsilon_{xy}\cos(2\theta)]\cos(\theta)}{1 - \epsilon_{xy}} \quad (1)$$

$$y = \frac{R_0[1 + \epsilon_{yz}\cos(2\varphi')]\sin\varphi'[1 + \epsilon_{xy}\cos(2\theta)]\sin(\theta)}{1 - \epsilon_{xy}} \quad (2)$$

$$z = R_0[1 + \epsilon_{yz}\cos(2\varphi')]\cos\varphi' \quad (3)$$

where $$\varphi' = \tan^{-1}\left[\frac{(1-\epsilon_{xy})\cot\varphi}{1+\epsilon_{xy}\cos(2\theta)}\right]. \quad (4)$$

$R_0$ is the mean cavity radius, $\epsilon_{xy}$ and $\epsilon_{yz}$ are the deformation parameters that determine the extent of the cavity deformation in the x-y and y-z planes. The deformation parameters jointly play an important role in shaping the chaotic cavity 100. If either $\epsilon_{xy}$ or $\epsilon_{yz}$ is zero, then the cavity 100 has rotational symmetry; the cavity 100 is then referred to as a rotationally symmetric chaotic (RSC) cavity. If both $\epsilon_{xy}$ and $\epsilon_{yz}$ are different from zero, then the cavity 100 has three degrees of freedom with a changing radius dependent on θ and φ, and is called a rotationally asymmetric chaotic (RAC) cavity herein.

Figure 1C:
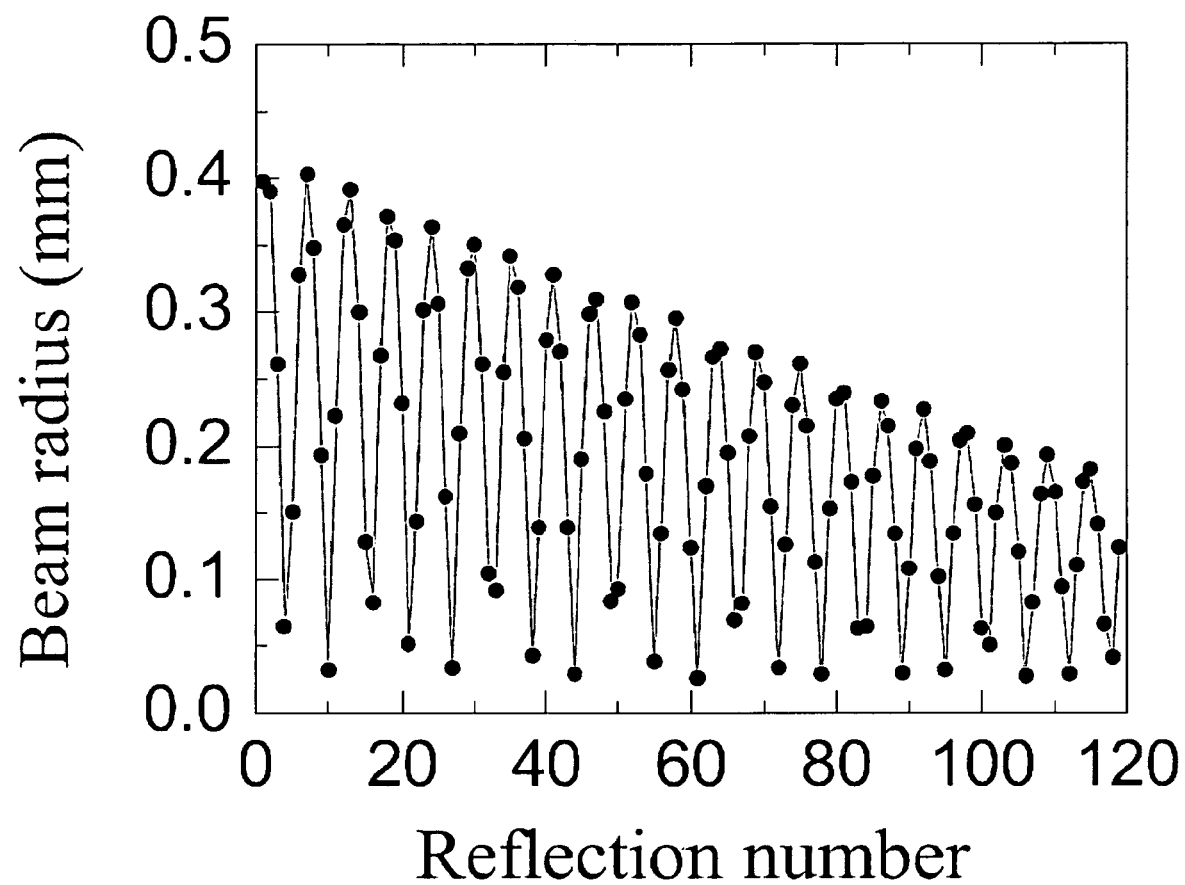
FIG. 1(c) illustrates the development of beam size as a function of reflection number.

The light beam may be coupled in and out through the same optical port 30, which is convenient as long as the direction of the outgoing beam is different from the direction of the input beam. Inside the cavity 100, the light beam bounces back and forth and traces out a spot pattern on the cavity surface 10. When big deformations are introduced into the spherical cavity 100, such as $\epsilon_{xy}$>>0.1 and $\epsilon_{yz}$>>0.1, the ray dynamics of the cavity 100 is fully chaotic, implying that the input beam rapidly diverges (or two input beams that only slightly apart rapidly separate from other) over the course of reflections. However, when small deformations are employed, such as $\epsilon_{xy}$=0.01 and $\epsilon_{yz}$=0.02, the cavity 100 can support quasi-chaotic ray dynamics in the phase space. Once a light beam is injected into the quasi-chaotic region, it will be confined within the same region for a long time, leading to limited beam divergence. Actually, with proper cavity parameters, the beam size decreases within the first 100 reflections. For example, FIG. 1(c) shows the calculated beam size versus the reflection number for a 118-pass orbit for a cavity having $\epsilon_{xy}$=0.01 and $\epsilon_{yz}$=0.02. The initial decrease in the beam size can be understood from a systematic point of view. One can decompose the chaotic cavity surface 10 into a series of unequally spaced thin lenses, each of which has a different focal length. With an appropriate input beam direction and first focus point, the beam is able to be focused after passing through hundreds of lenses. Depending on the direction of the ray as it enters the cavity 100, there are numerous patterns of possible ray trajectories.

To explore the cavity behavior under various deformation parameters, the ray dynamics were modeled in the chaotic cavity 100 using a two dimensional iterated map. Let $p_i=(x_i, y_i, z_i)$ denote the beam spot position and $q_i=(\theta_i, \phi_i)$ be the beam direction of one trajectory after reflections. The ray dynamics, i.e., spot position and beam direction, can be iteratively computed as $$(p_{i+1}, q_{i+1})=F(p_i, q_i, u) \quad (5)$$

where u is the cavity 100 parameter. Thus, $F^n(p, q, u)$ represents the nth recursion of F(p, q, u). An orbit under map F is the set of points and directions According to the multi-pass cell requirements, a chaotic cavity 100 has the desired properties if it satisfies the following conditions:

(i) $\|p_n-p_0\|_2 \leq s$ and $q_n \neq q_0$ (ii) $\|p_i-p_0\|_2 \geq 5w$, if $i \neq n$ (iii) $\|p_i-p_j\|_2 > 2w$, if $i \neq j$ and $\{i,j\} \neq \{n, 0\}$ (iv) $\|\delta p_n\|_2 \leq s$, when $(p_n+\delta p_n, q_n+\delta q_n) = F^n(p_0+\delta p_0, q_0+\delta q_0, u)$ (6)

where $\|\cdot\|_2$ denotes the $l_2$ norm, s represents the radius of the optical port 30 used to send the light into and extract it out of the cavity 100, w stands for the input beam radius, $(p_0+\delta p_0, q_0+\delta q_0)$ are the initial conditions of an orbit with a small disturbance, and $\delta p_0$ and $\delta q_0$ represent the difference between this orbit and the initial one in the starting point and direction, as shown in FIG. 1(b).

These conditions have important physical implications. Condition (i) states the re-entrant condition: after n reflections, a ray returns to its entrance point $p_0$ with a distance smaller than the optical port radius, provided that the optical port 30 is centered at $p_0$. Furthermore, the direction of the out-coupling beam should be different from the direction of the input beam. Condition (ii) requires that all other beam spots be far from the center of the optical port 30 at $p_0$. The separation between the closest neighboring spot to $p_0$ should be greater than 5 times the input beam radius, as a practical choice. Condition (iii) defines the criterion that the separation between any two beam spots (except the input and output beams) should be at least twice the input beam radius. This requirement reduces the beam overlap at the cavity surface 10, assuming that the beam spot does not grow beyond two times the initial beam size. Condition (iv) dictates the orbital stability in the sense that all the nearby orbits having initial conditions in a "cone" of $\delta p_0$ and $\delta q_0$ will be coupled out of the optical port 30 after n iterations. Because the laser beam is focused into the cavity 100 in the actual system, $\|\delta p_0\|_2$ implies the input beam radius and $\delta q_0$ represents the beam divergence. Next, the dynamics in the RAC and RSC cavity 100 are analyzed in terms of the four conditions in (6).

Figure 2A:
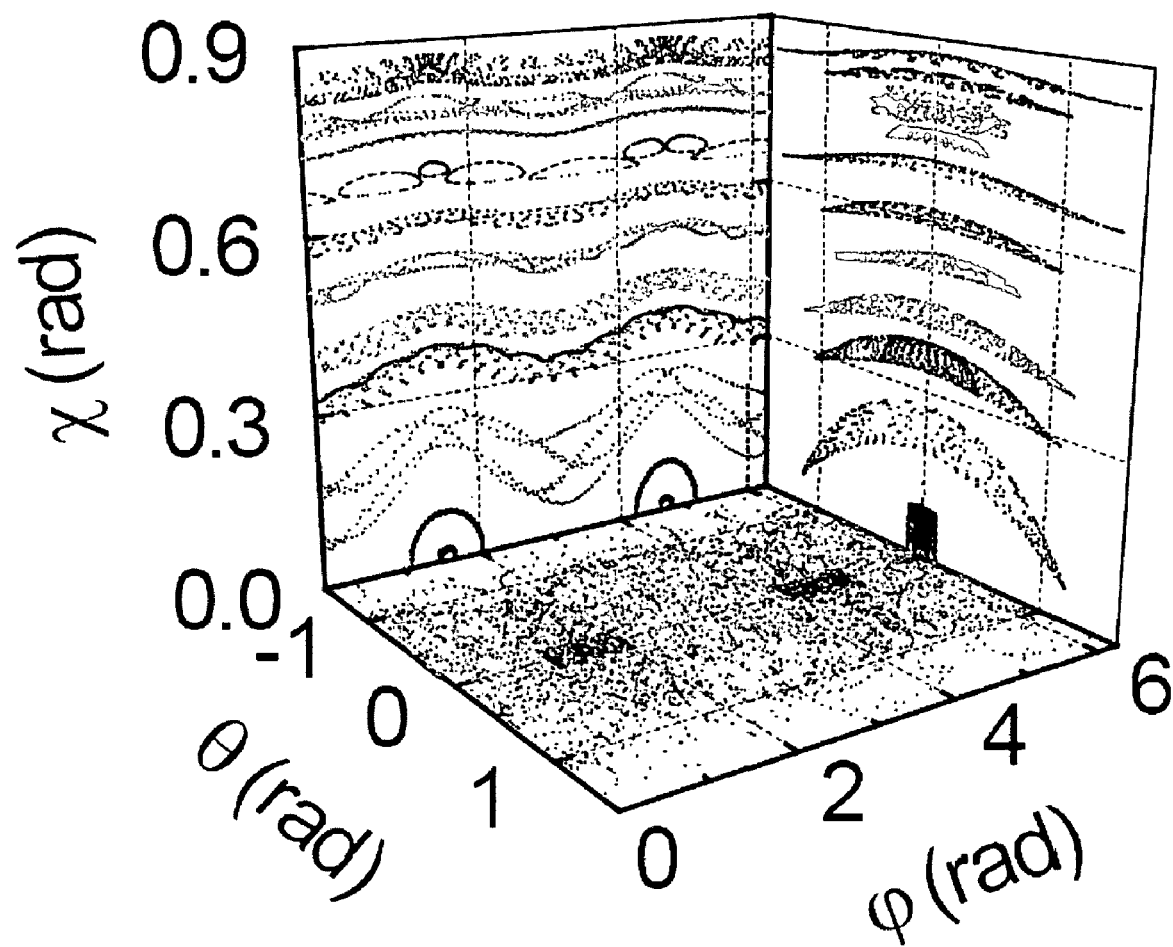
FIG. 2(a) illustrates ray trajectories in phase space projected onto three different planes for an asymmetric chaotic cavity having $\epsilon_{xy}=0.01$ and $\epsilon_{yz}=0.02$, with the gray trajectories launched into the cavity from the point ($\theta=\pi/2$, $\phi=0.1745$) and the black trajectories injected from the position ($\theta=\pi/2$, $\phi=0$)
Figure 2B:
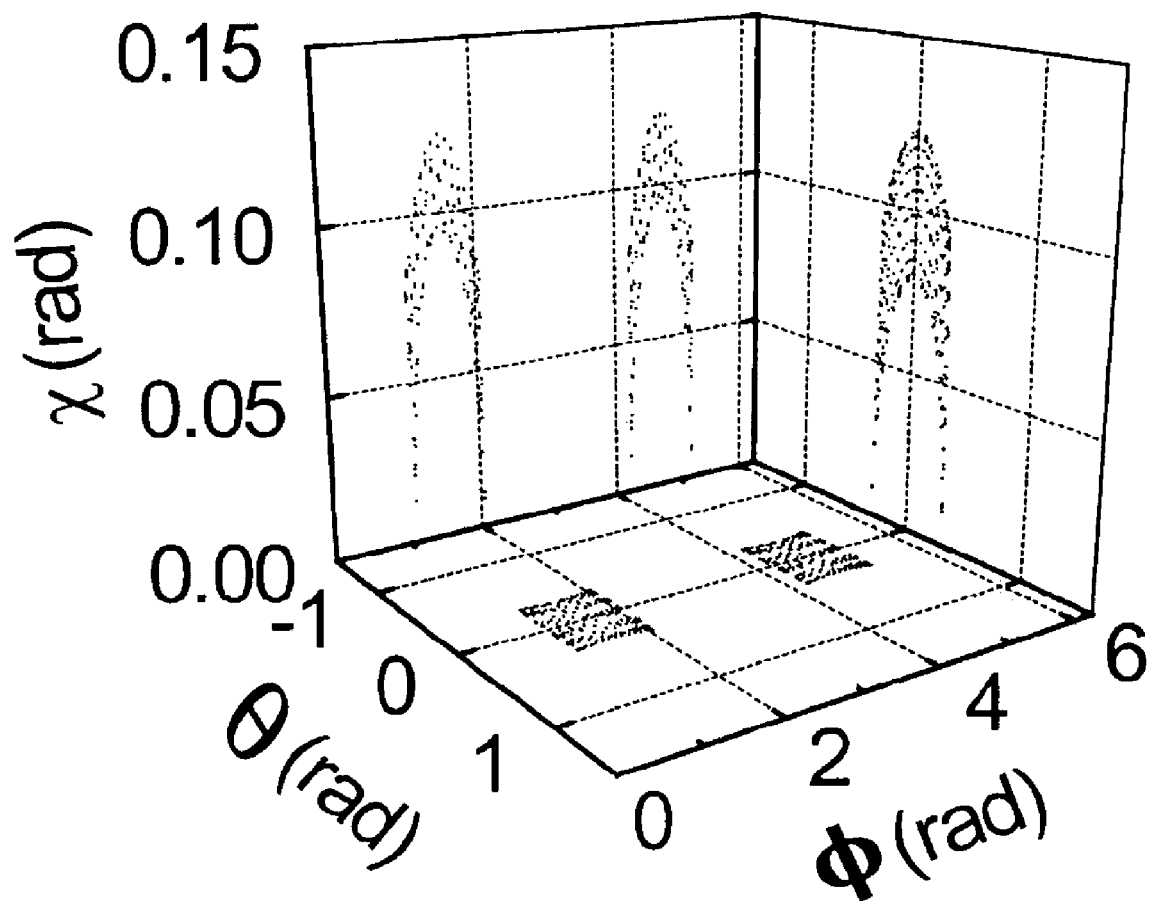
FIG. 2(b) illustrates the corresponding reflection points for the trajectories of FIG. 2(a) launched into the cavity from the position ($\theta=\pi/2$, $\phi=0$)

It can be shown that the ray dynamics becomes more chaotic with increasing deformation. In the extreme case $\epsilon_{xy} \gg 0.1$ and $\epsilon_{yz} \gg 0.1$, the ray orbit rapidly repels all its neighboring trajectories. As a consequence, for a multi-pass RAC cavity 100 where a long term stable orbit is desired, it is expected that the cell has a small deformation. FIG. 2 presents the Poincaré surface of sections (SOS) of 15 trajectories in a cavity 100 with $\epsilon_{xy}=0.01$ and $\epsilon_{yz}=0.02$, started at different initial conditions. Here, the Poincaré SOS is plotted by recording the angle of incidence $\chi$ as a function of $\theta$ and $\phi$ for each reflection. The resulting trajectories illustrate the chaotic features, but some of them are still confined within the specific regions in $(\theta, \phi)$ space after 400 reflections. Because the trajectory should not enter the junction regions of the two shells at $\theta=0$, an orbit with a shape of a "double arch" shown in the $\theta$-$\chi$ plane was selected.

Figure 3A:
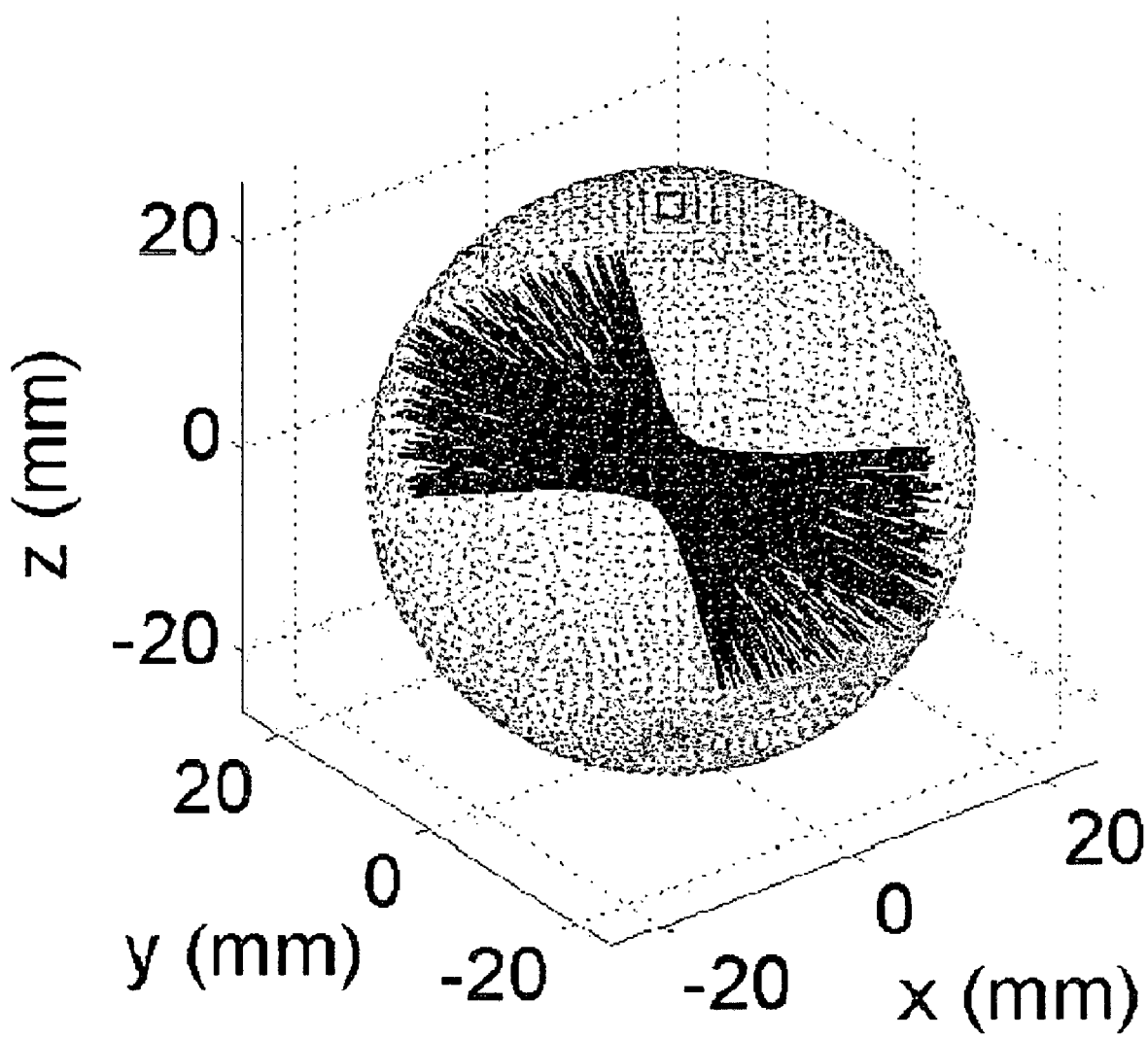
FIG. 3(a) illustrates the 3-D geometry and ray trajectories of a rotationally asymmetric chaotic cavity with $\epsilon_{xy}=0.01$ and $\epsilon_{yz}=0.02$.

Among those double arch trajectories, an orbit satisfying all the conditions in (6) is numerically calculated using the recursive method in the RAC cavity 100. $R_0=25.4$mm, s=1.1 mm, and w=0.47 mm, and a laser wavelength less than or equal to 6 μm were chosen such that the input laser Gaussian beam could be approximated as a spherical wave. Let the orbit have a starting position $p_0=(0, 24.89, 0)$ mm and an input direction $q_0=(-1.4837, 0.0873)$ rad. The bounded motion in real space is shown in FIG. 3(a), and the corresponding reflection points in phase space are plotted in FIG. 2(b).

Figure 4A:
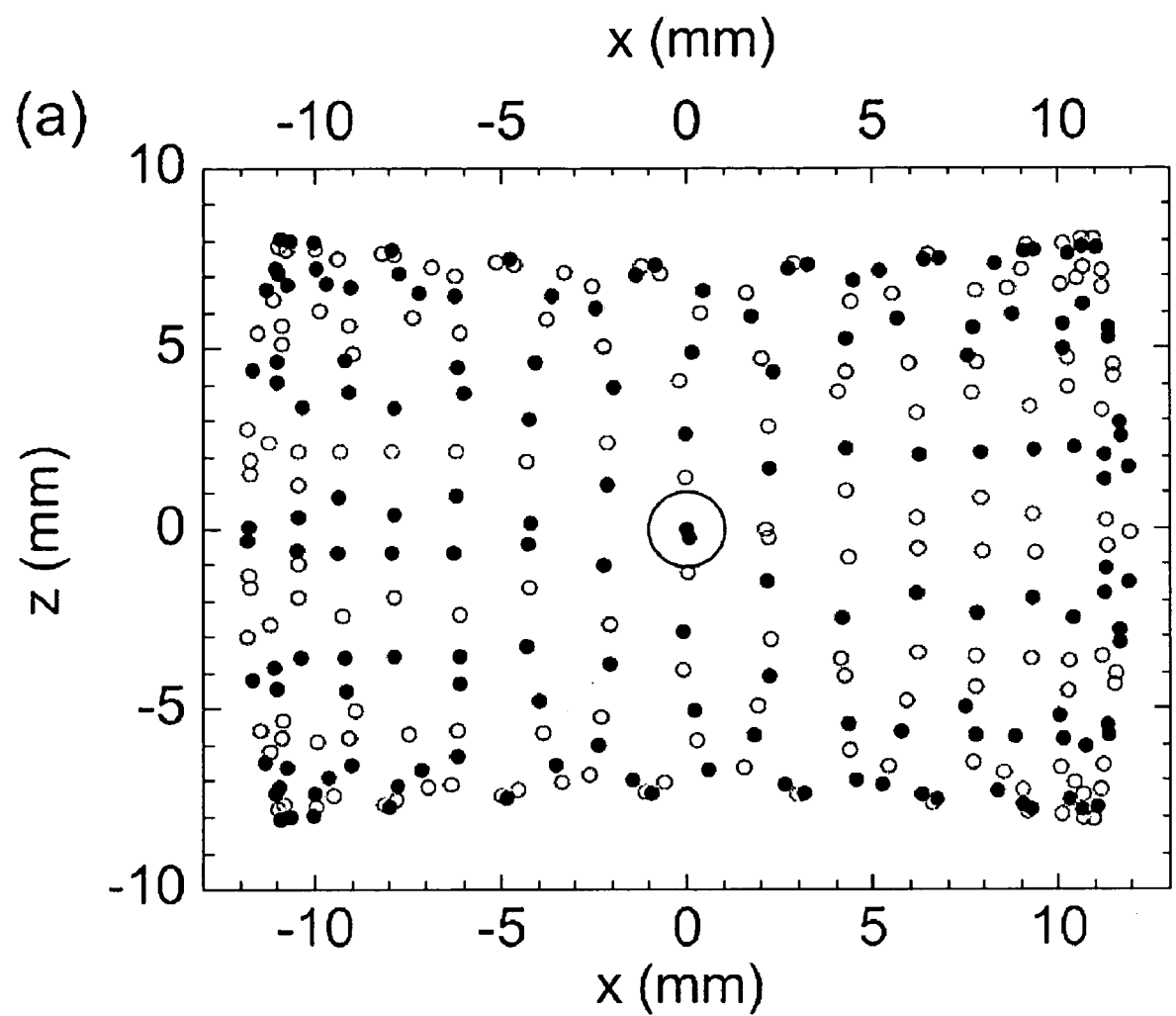
FIGS. 4(a) and 4(b) illustrate the spot distribution in the chaotic cavity on the input cavity wall y>0 (filled circles) and the opposite wall y<0 (open circles) in x-z coordinates and on both walls in y-z coordinates, respectively.
Figure 4B:
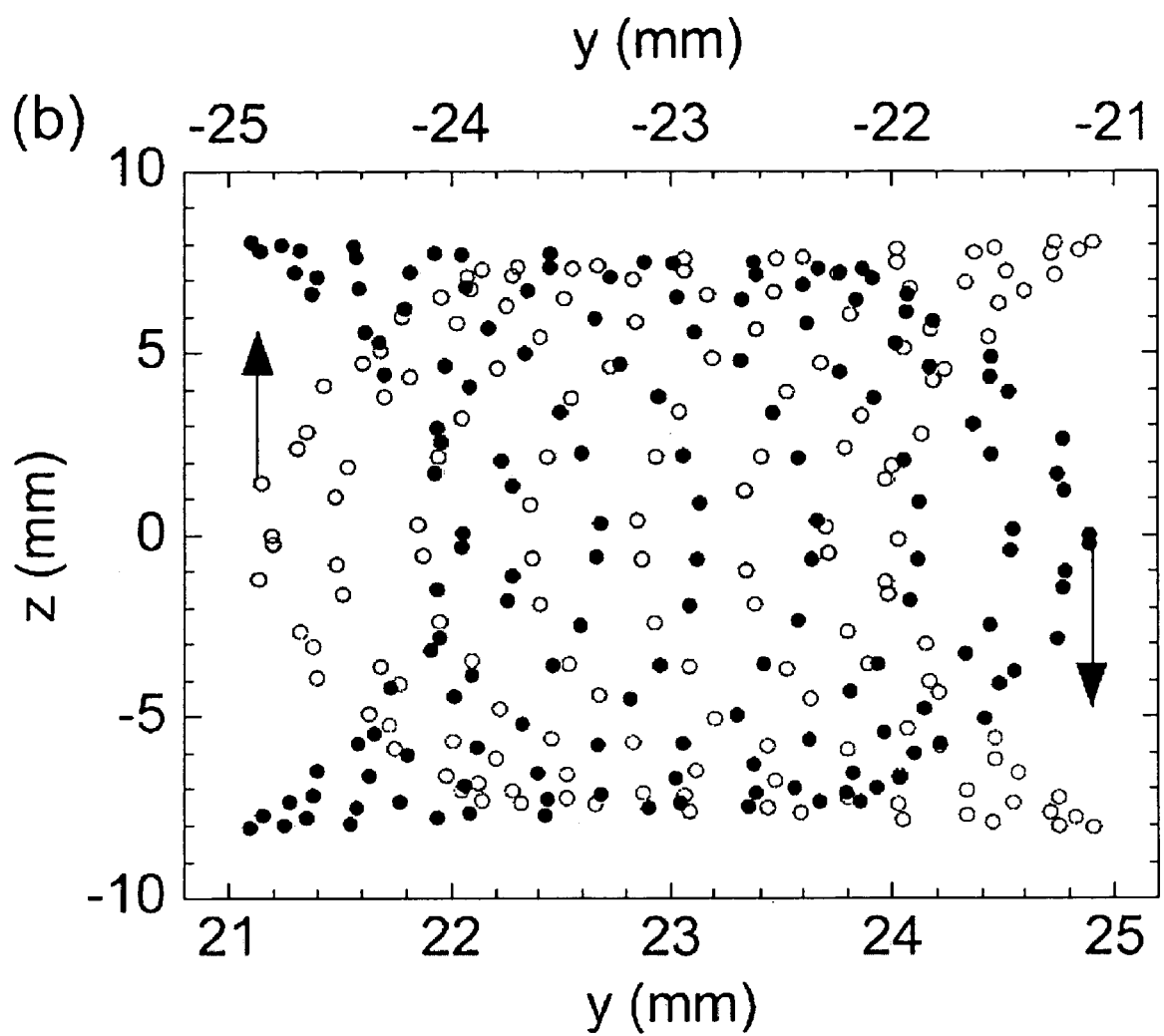
Figure 4C:
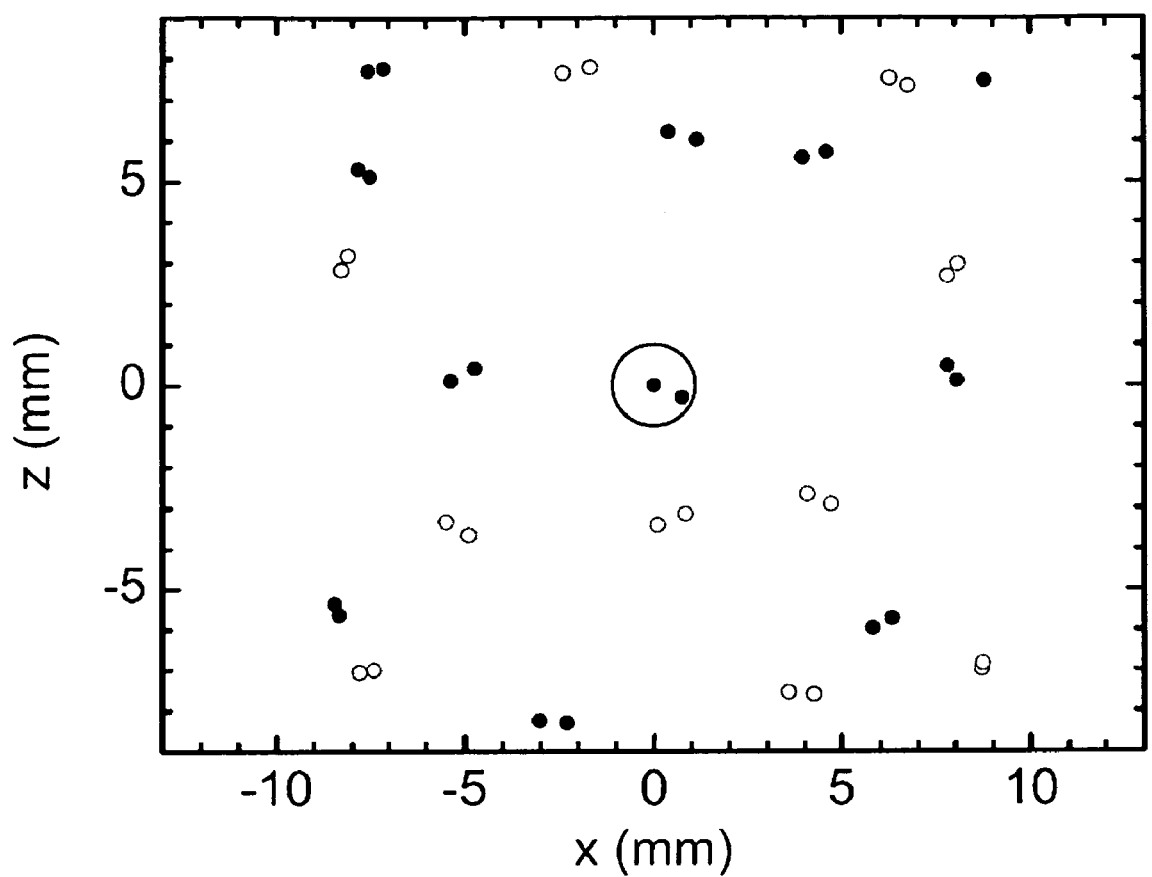
FIG. 4(c) illustrates the spot distribution in the chaotic cavity on the input cavity wall y>0 (filled circles) and the opposite wall y<0 (open circles) in x-z coordinates for a 40-pass orbit.

To illustrate how the spots are distributed on the cavity surface 10, FIGS. 4(a) and 4(b) show the projection of $p_i$ on the x-y and y-z planes, respectively. The solid dots indicate the beam spot with y>0, whereas the open circles represent the spots corresponding to y<0. While the beam spots are uniformly distributed within a rectangular boundary on the cavity surface 10, the ray returns to the optical port 30 (large circle) after 306 reflections, meeting the re-entrant condition. The distance between the innermost spot and the optical port center is 2.4 mm (5.1×w), which is comparable to the corresponding distance in a conventional 168-pass multi-pass cell. Also, the smallest distance between two neighboring spots on the cavity surface 10 is 0.22 mm (about 2.2×w). The total optical path length inside the cavity 100 is 15.5 meters. For a 40-pass pattern shown in FIG. 4(c), the distance between the innermost spot to the optical port center is 4.78 mm, the smallest distance between two neighboring spots on the cavity surface 10 is 0.15 mm, and the count optical path length is about 2 m. This low-pass pattern was used to test the prototype multi-pass cell with a red diode laser as detailed below.

In order to evaluate the stability of this trajectory, the Euclidean distance is calculated between the spots on an orbit $\{(x'_0, y'_0, z'_0), (x'_1, y'_1, z'_1), \ldots\}$ and those on an initial orbit $\{(x_0, y_0, z_0), (x_1, y_1, z_1), \ldots\}$. In particular, the distance projected on the x-z or x-y plane is $$dh_i = \begin{cases} \sqrt{(x_i - x'_i)^2 + (z_i - z'_i)^2} & \text{for an } RAC \text{ cavity} \\ \sqrt{(x_i - x'_i)^2 + (y_i - y'_i)^2} & \text{for an } RSC \text{ cavity} \end{cases} \quad (7)$$

and the orbit separation along y-axis is $$dv_i = \begin{cases} y_i - y'_i & \text{for an } RAC \text{ cavity} \\ z_i - z'_i & \text{for an } RSC \text{ cavity}. \end{cases} \quad (8)$$

Figure 5A:
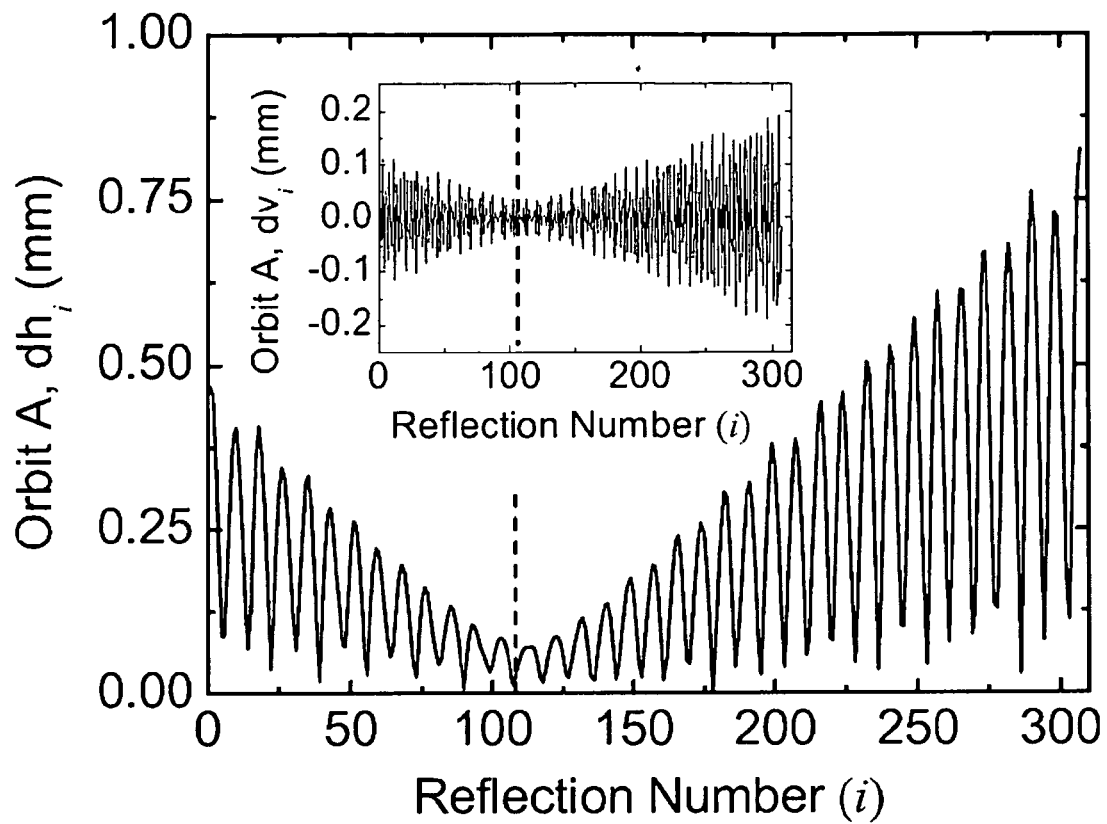
FIGS. 5(a) and 5(b) illustrate the evolution of the beam size as expressed by $dh_i$ for orbit A and orbit B in the rotationally asymmetric chaotic cavity of FIG. 3(a), respectively, with the insets showing $dv_i$ for orbits A and B, respectively.
Figure 5B:
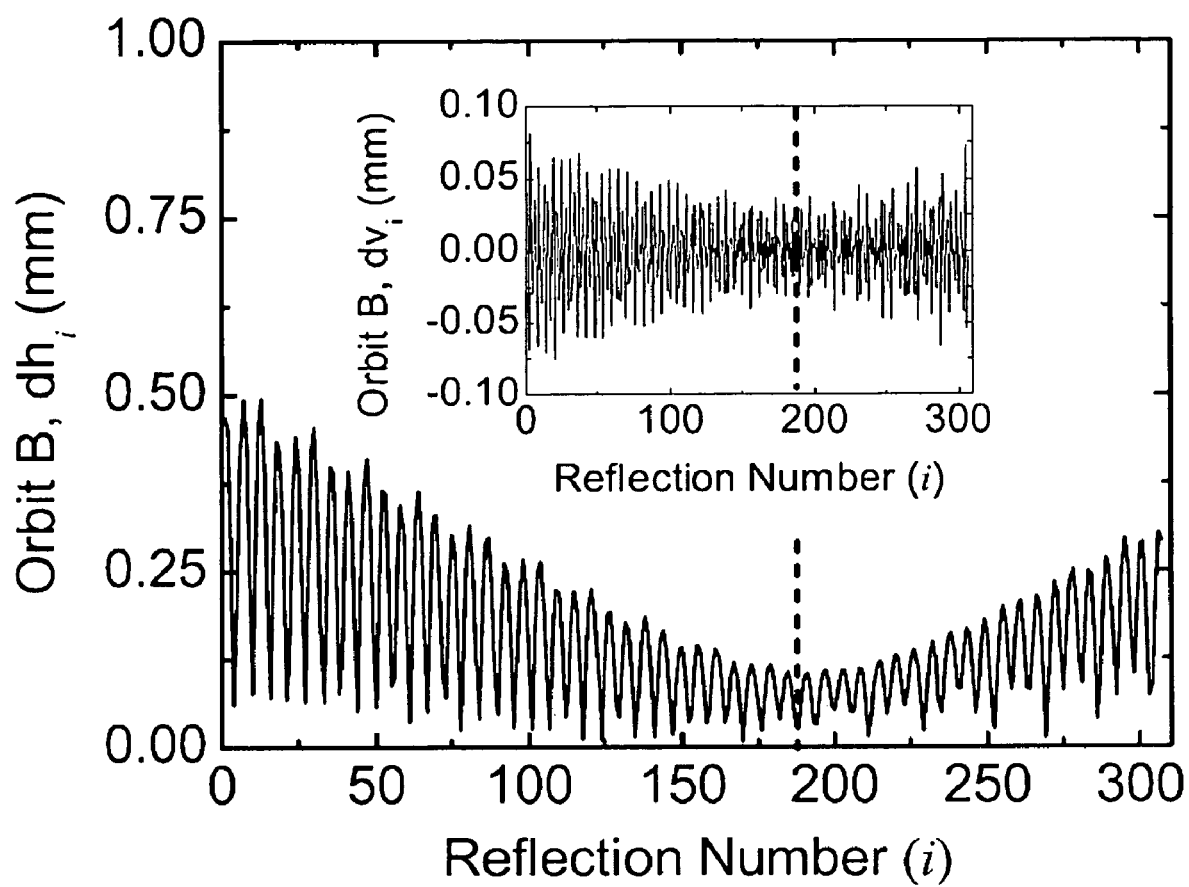

Two orbits A and B were considered. With respect to the initial orbit $\{(p_0, q_0), (p_1, q_1), \ldots\}$, orbit A has the initial conditions as $\delta p_0=(0.4681, 0.0409, 0)$ mm and $\delta q_0=0.0221,-5.8\times10^{-5}$) rad, while orbit B is defined by $\delta p_0=(-0.0036, 0.0408, 0.4681)$ mm and $\delta q_0=(-0.00017,-0.0218)$ rad. The numerical results of A and B are shown in FIGS. 5(a) and 5(b), respectively. In FIG. 5(a), the envelopes of the oscillating $dh_i$ and $dv_i$ first decrease, and then increase with a minimum value occurred at a global focus time (GFT), which is indicated as dashed lines. The initial shrinking of $dh_i$ when fitted with an exponential corresponds to a negative Liapunov exponent (negative beam diverging rate) $\lambda_n \approx -0.017$. When i is greater than the GFT-turning point ($\approx 108$), the envelope of $dh_i$ grows with a positive Liapunov exponent (positive beam diverging rate) $\lambda_p \approx 0.013$. Similar dynamics is observed in $dh_i$ and $dv_i$ for orbit B, where the amplitude fluctuates with a 50% higher oscillating frequency and a larger GFT value ($\approx 188$).

The oscillating behavior of $dh_i$ and $dv_i$ is due to the inherent characteristics of a concave surface that refocuses the beam. Since the cavity 100 is rotationally asymmetric, orbits A and B will experience two different focusing systems and the resulting GFTs will be different. For i>GFT, the beam begins to diverge due to the intrinsic property of a chaotic cavity 100: two orbits with different initial conditions will diverge from each other for $i \gg \lambda_p^{-1}$. However, it is found that the value of GFT or chaos can be controlled by the focus point of the input beam and the deformation parameters. In order to reduce the beam divergence, a focus point is selected such that the value of GFT is as large as possible. In this example, with a GFT around 108, the beam size increases to around 1.8 mm after 306 reflections, which is still smaller than the optical port size (2.2 mm). Furthermore, a variety of spot patterns and path lengths are accessible by changing the injected beam direction with the same optical port 30.

The ray dynamics of the RSC cavity is quite different from that of the RAC cavity. Due to the rotational symmetry, the z component of the angular momentum L is conserved in the ray dynamics of an RSC cavity 100; therefore, the phase-space motion of a ray trajectory can be parameterized by the conserved value of $L_z$.

Figure 3B:
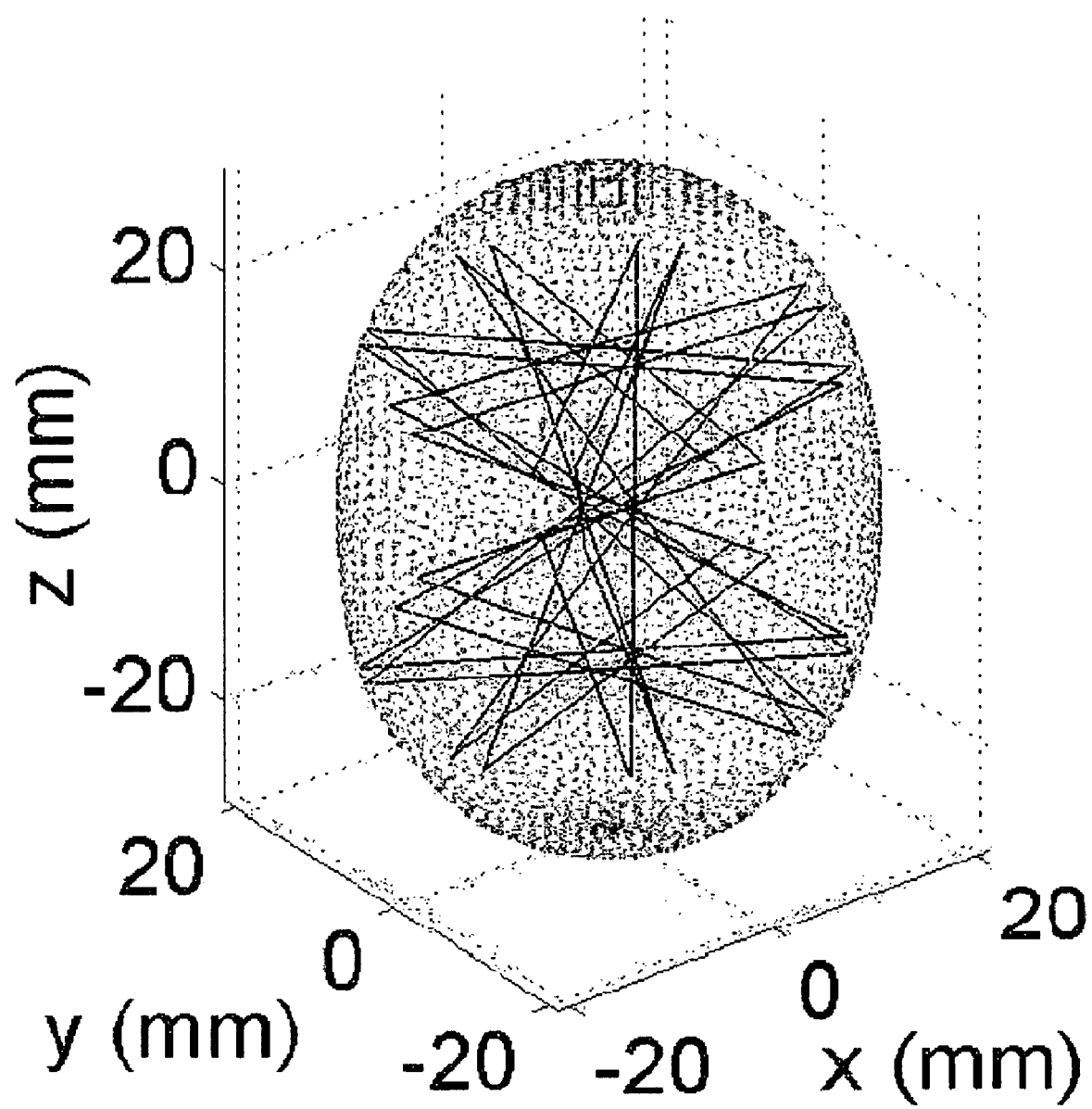
FIG. 3(b) illustrates the 3-D geometry and ray trajectories of a rotationally symmetric chaotic cavity with $\epsilon_{xy}$=0 and $\epsilon_{yz}$=0.16.
Figure 6A:
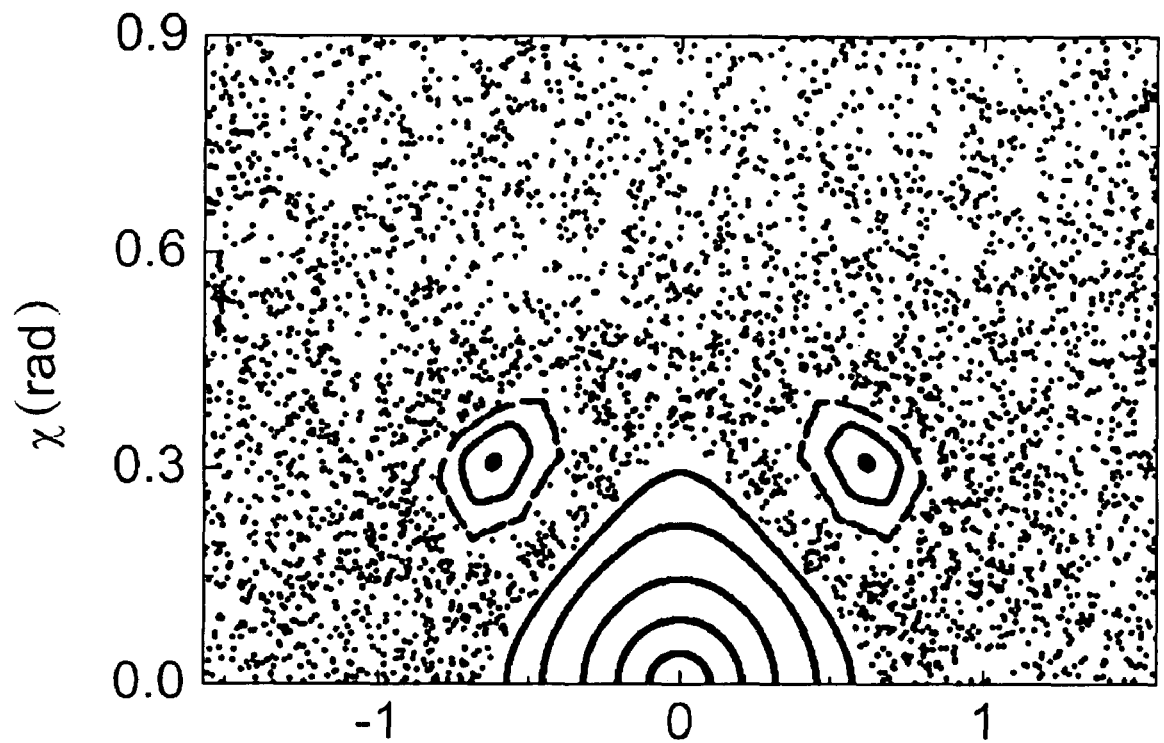
FIGS. 6(a), 6(b), and 6(c) illustrate the Poincaré surface of section for the rotationally symmetric cavity of FIG. 3(b) for $L_z$=0, $L_z$=0.013, and $L_z$=0.16, respectively.
Figure 6B:
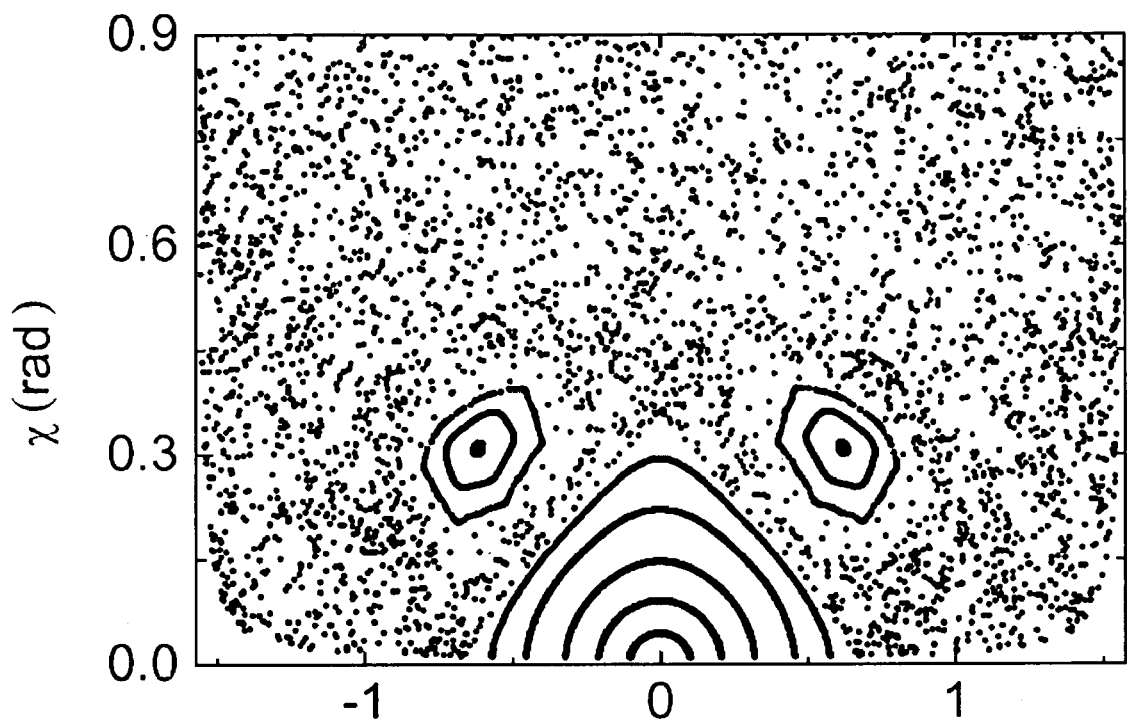
Figure 6C:
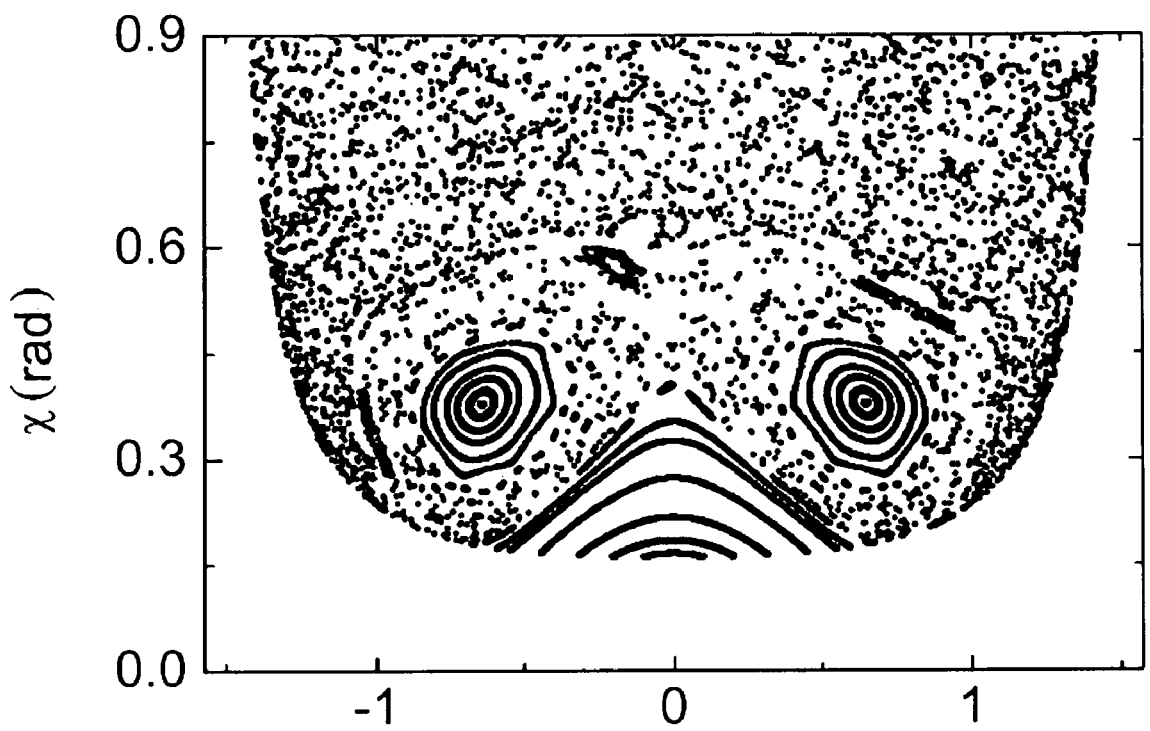

FIGS. 6(a)-(c) shows the Poincaré SOS for a cavity 100 with deformation of $\epsilon_{xy}=0$ and $\epsilon_{yz}=0.16$, for increasing $L_z$. The RSC cavity 100 can support stable bowtie orbits at various $L_z$ values. The ray trajectories cannot traverse between the stable and chaotic regions, hence an orbit will remain trapped within the region where it initially starts. For rays that have various $L_z$ values, as long as they are coupled into the stable bowtie regions, the distances between them are limited by the size of the island in the θ direction. However, due to the cylindrical symmetry of the cavity 100, orbits that have different $L_z$ diverge from each other along the φ direction. For example, FIG. 3(b) shows the ray trajectory generated in the experiment with an initial condition $p_0$=(13.9073, 13.9073, 13.7716) mm, $q_0$=(−2.4435, 0), and $R_0$=25.4 mm. The ray follows a "bow-tie" orbit as it rotates around the z axis with an angular momentum $L_z$=0.08. The optical path length is 1.5 meters. Like the two orbits in the RAC cavity 100, orbit A in RSC cavity 100 has a deviation $\delta p_0$=(0.302, −0.360, 0) mm and $\delta q_0$=(−0.022, 0) rad, while B is the perturbed orbit with $\delta p_0$=(0, 0, 0.470) mm and $\delta q_0$=(−5.1×10$^{-5}$, −0.022) rad. The $L_z$ of the reference orbit is the same as that of orbit B, while being different from orbit A.

Figure 7A:
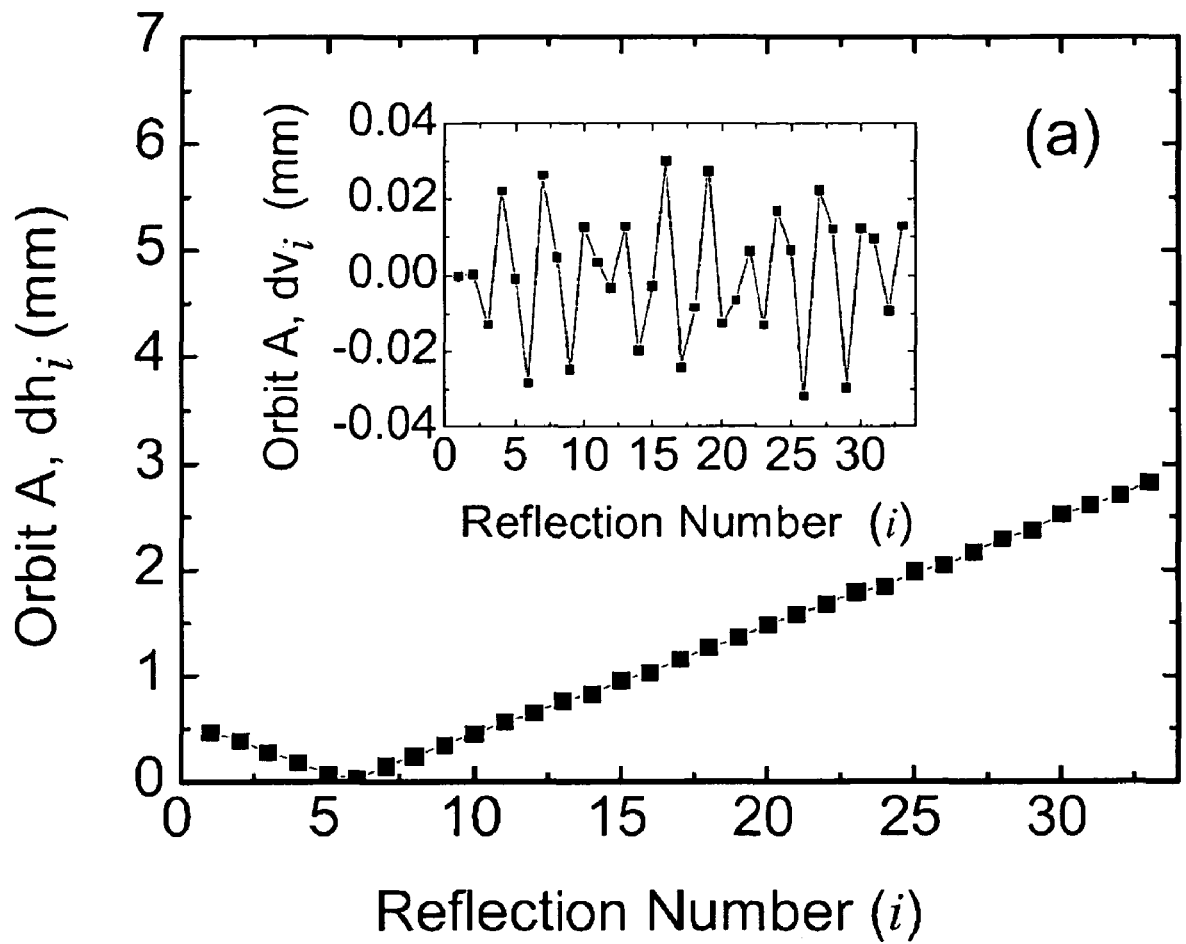
FIGS. 7(a) and 7(b) illustrate the evolution of the beam size as expressed by $dh_i$ for orbit A and orbit B, respectively, for the rotationally symmetric cavity of FIG. 3(b) with the insets showing $dv_i$ for orbits A and B, respectively.
Figure 7B:
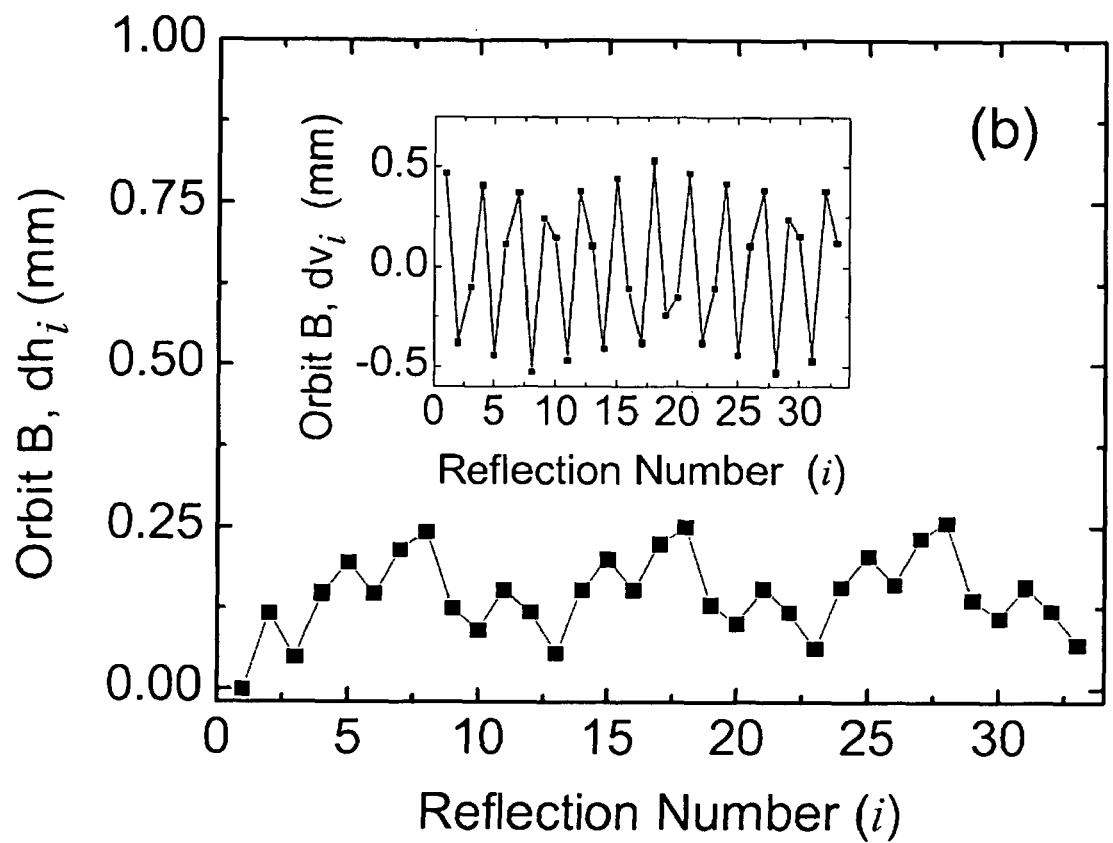

The corresponding $dh_i$ and $dv_i$ derived from the two orbits are shown in FIGS. 7(a) and (b), respectively. (Note that the reflection number is 10 times smaller compared to FIG. 5) For an RSC cavity 100, the ray trajectories cannot traverse between stable and chaotic regions, thus an orbit will remain trapped within the region where it initially starts. However, due to the cylindrical symmetry of the cavity 100, an orbit that deviates slightly from the reference orbit along the direction perpendicular to the z axis, such as A, experiences a quite different ray dynamics. As clearly seen in the insets of FIGS. 7(a) and 7(b), the beam spot size is almost unchanged with reflection numbers in the φ direction. In the θ direction, although both the reference orbit and A are stable and quasi-periodic, their difference $dh_i$ increases to 3 mm after 32 reflections, while the $dh_i$ value for the reference orbit and B is almost constant within the initial 32 reflections. The above calculation agrees well with the experimental observation.

EXAMPLES

The utility of the rotationally asymmetric chaotic multi-pass cavity 100 in accordance with the present invention was demonstrated experimentally. For this first example, the chaotic multi-pass cavity 100 was fabricated from a copper substrate with $R_0$=2.54 cm, $\epsilon_{xy}$=0.01, and $\epsilon_{yz}$=0.02. The cavity 100 consisted of two half shells 22, 24 shaped by a traditional milling process, which had a manufacturing accuracy of about 5.1 μm in the cavity radius. Afterwards, a Ti/Au (300/3000 Å) coating was deposited onto the inner polished cavity surface 10 by e-beam evaporation. Two such shells 22, 24 were manufactured and fastened to each other permanently to yield the structure illustrated in FIG. 1(a). A 2 mm diameter aperture was drilled at the front cavity shell 22 to provide the optical port 30 for light to be coupled in and out. The gas inlet and outlet ports 42, 44 were located at the top and bottom ends of the cavity 100 so that the ports 42, 44 did not interfere with the circulating light rays and the optical port 30.

Figure 8A:
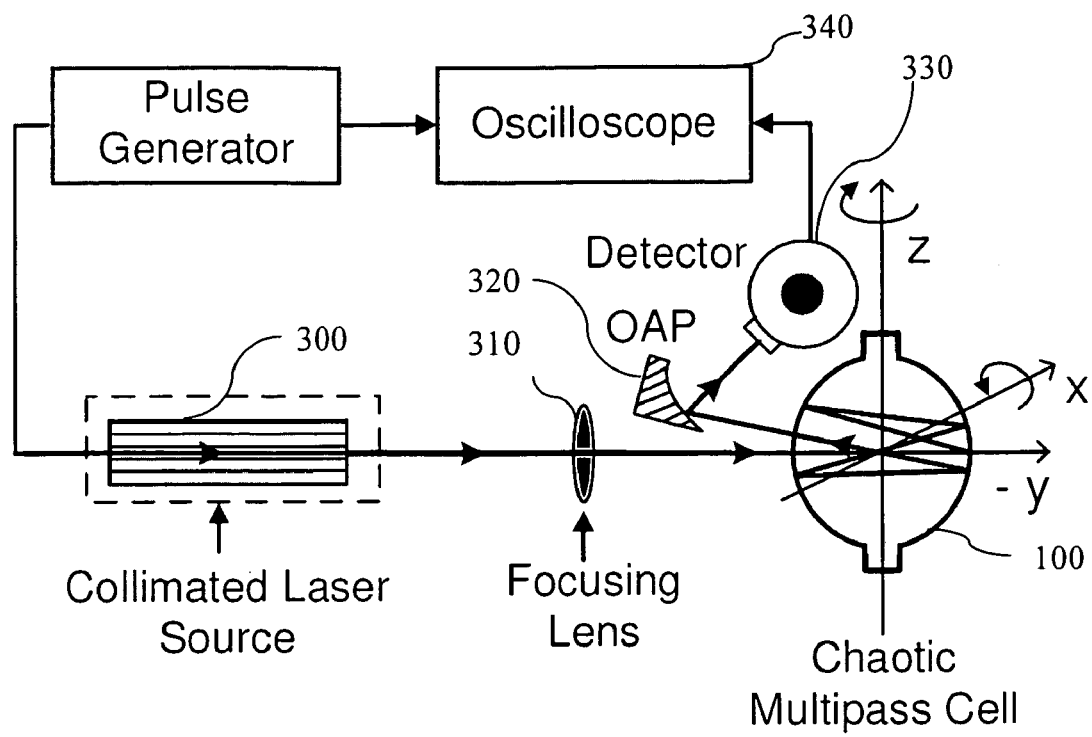
FIGS. 8(a) and 8(b) schematically illustrate experimental setups for pulse delay measurement of chaotic multi-pass cavities in accordance with the present invention.

The experimental pulse-delay setup used to characterize the cavity 100 is illustrated schematically in FIG. 8(a). A Daylight Solutions 10102 QC laser 300 emitting around 10 μm was employed as the source. The laser 300 was operated with a pulse width of 100 ns, a pulse repetition rate of 99.7 kHz, and a peak output power of around 60 mW. The collimated laser beam was focused on the x-z center plane of the cavity 100 through a Ge lens 310 with a focal length of 4 in. The focused Gaussian beam had a diameter of 0.80 mm in the horizontal direction and 0.84 mm in the vertical direction at the 2 mm diameter optical port 30. The cavity 100 was mounted on a rotation stage on top of an x-y-z translation stage to allow light to be injected into the cavity 100 in an arbitrary direction. Specifically, the cavity 100 could be rotated around the z and x axes. Finally, an off-axis parabolic (OAP) mirror 320 focused the light coupled out of the cavity 100 onto a high-speed HgCdTe detector 330 with a rise time of about 1 ns. The amplitude and temporal profile of the detector signal were recorded by a digital oscilloscope 340.

In order to measure the optical path length in the cavity 100, the spot patterns and optical path lengths were first simulated, and then the corresponding beam input directions were set in the setup to detect the temporal envelope and intensity of the pulses coupled out of the cavity 100. Next, the input pulse was measured directly without entering the cavity 100, using a parabolic mirror and the same detector 330. By measuring the time delay between the pulse coupled out of the cavity 100 and the pulse directly from the laser 300, the optical path length was obtained at the specified input beam direction.

Figure 10:
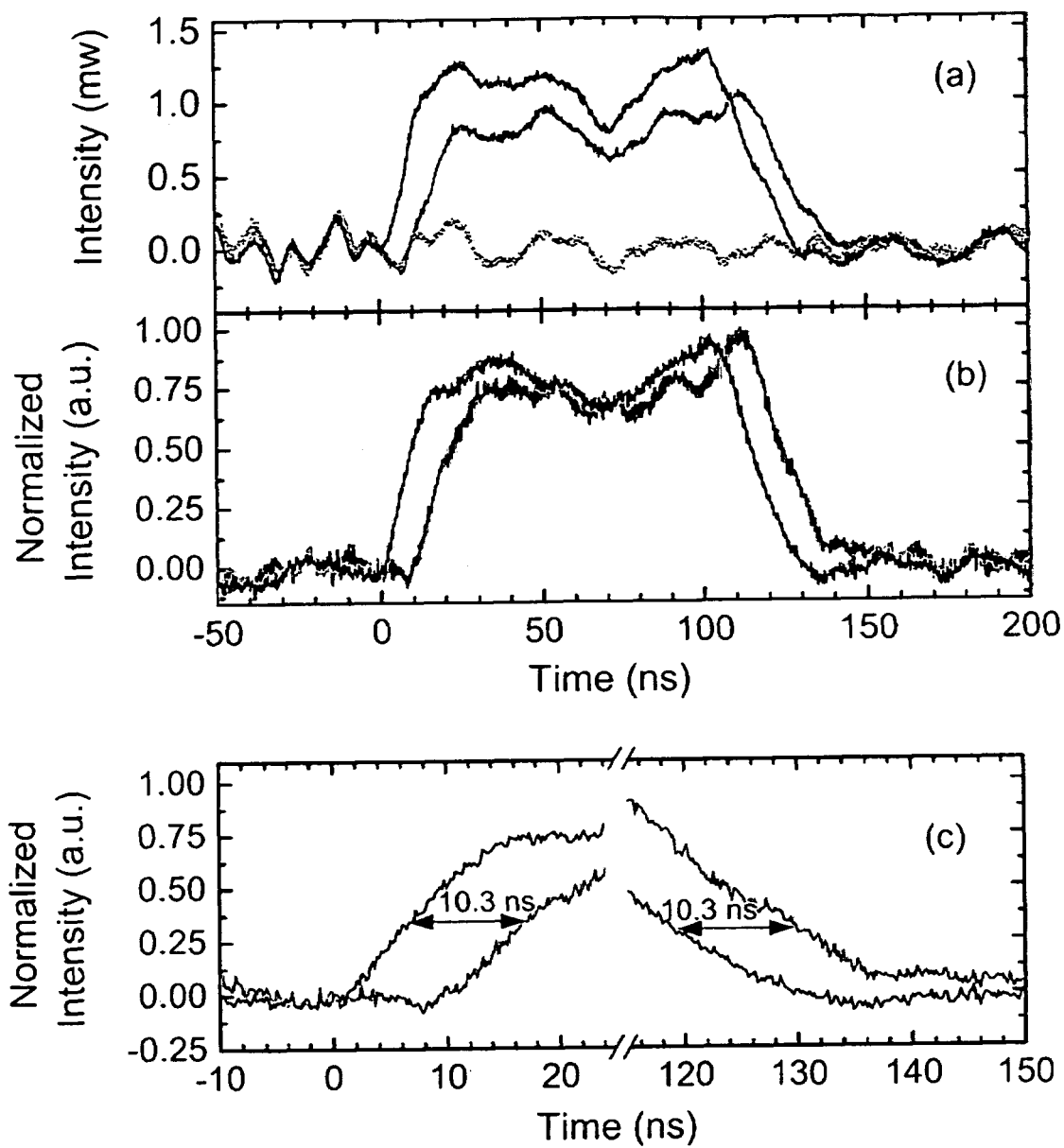
FIG. 10(a) illustrates intensity versus time of the out-coupled light pulse (gray), the reference input pulse (black), and the background noise floor (dotted)
FIG. 10(b) illustrates the normalized pulse height of the pulses in FIG. 10(a) after subtracting the background.
FIG. 10(c) illustrates the time delay on the rising and the falling edge between the outcoupled and the reference pulses in FIG. 10(b) as 10.3 ns, corresponding to an optical path length of 3.1 m.

In a first experiment, the cavity 100 was angled at θ=1.5° and φ=4.5° with respect to the x and z axes, respectively, corresponding to the input beam direction for a 62-pass trajectory. A 10.3 ns time delay was measured between the multi-pass and the directly reflected pulse, which corresponded to a 3.1 m path length with a measurement accuracy of 0.06 m. FIG. 10(a) shows the pulse data where the pulse coupled from inside the cavity 100 is plotted in gray, the reference pulse without entering the cavity 100 in black, and the background detector signal obtained without light pulses in dots. In order to make the reference signal have about the same signal to noise ratio as that of the multi-pass signal, the reference pulse was attenuated by focusing only part of a laser beam onto the detector 330. It was experimentally verified that the reference pulse with different light intensity had the same start time and rising edge after normalization. After subtracting the background noise floor, the normalized multi-pass signal and the reference signal are shown in FIG. 10(b). A close up of the pulse rising and falling edges is shown in FIG. 10(c).

Figure 11:
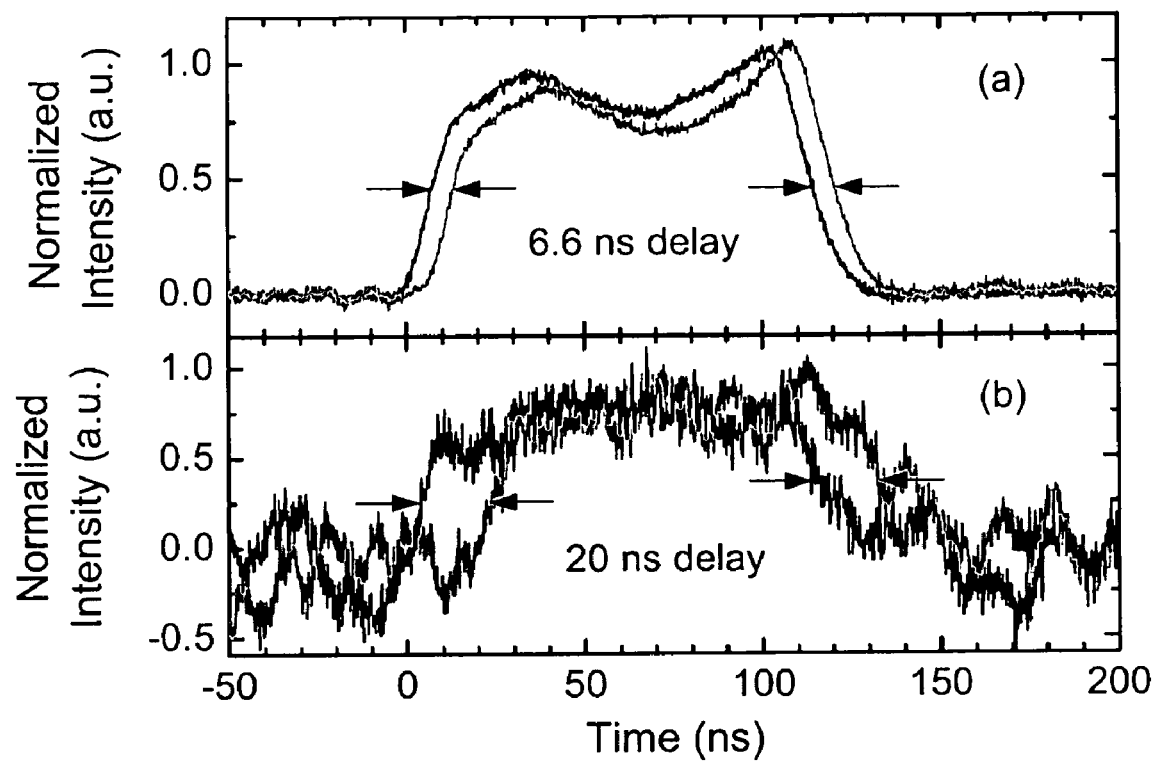
FIGS. 11(a) and 11(b) illustrate temporal pulse measurements for two different multi-pass trajectories, with the time delay between the out-coupled light pulse (gray) and the reference light pulse (black) being 6.6 ns and 20 ns, respectively, resulting in 2.0 and 6.0 m of optical path length, respectively, where the pulse amplitudes are normalized after subtracting the background noise floor.

A variety of shorter and longer path lengths were found in further experiments by adjusting the cavity 100 in the azimuthal and elevational directions. A multi-pass cavity that is able to support various optical patterns is useful for gas sensing applications where multiple path lengths are desired within the same cavity. In FIG. 11, the normalized pulse data for two other different optical path lengths are shown, with the detector noise subtracted. As seen in FIG. 11(a), the 6.6 ns time delay, corresponding to a 2.0 m path length, was measured between the reference and the multi-pass signal. In FIG. 11(b), a 20 ns time delay was observed, corresponding to a 6.0 m path length. The 2.0 and 6.0 m path lengths were observed with the cavity 100 angled at θ=3°, φ=5.5°, and θ=2.2°, φ=4.3°, respectively. For these three ray trajectories, a mixture of different path lengths were not observed, as shown by the shape similarity of the input and output pulse shapes. Interference fringes that a small multi-pass cell typically suffers cannot be tested by the current setup, due to the noise level of the pulsed QC laser 300.

The observed optical path lengths could be associated with the number of passes in the cavity 100, showing that the 2.0, 3.1, and 6.0 m path length undergoes 40, 62, and 118 reflections in the cavity 100, respectively. A very close match was achieved between the observed and simulated optical path lengths for these ray trajectories, confirming the predicted ray dynamics and the ability of the chaotic multi-pass cavity 100 to support meter-scale path lengths. For 2.0, 3.1, and 6.0 m optical paths, the calculated distances between the nearest spot (other than the outcoupled beam) to the center of the optical port 30 were 5.2, 2.4, and 1.9 mm, respectively, predicting that no shorter optical paths would be mixed with the desired optical paths. It was also calculated that the output light was directed with respect to the optical port 30 at $\theta=-92.7°$, $\phi=-3.8°$ for the 2.0 m path, $\theta=-87.5°$, $\phi=5.5°$ for the 3.1 m path, and $\theta=-91.3°$, $\phi=-5.0°$ for the 6.0 m path.

Moreover, the light intensity as a function of the reflection number was measured to examine the surface reflectivity of the Au/copper mirror. At 10 μm wavelength, the measured power levels of the light coupled out of the cavity 100 after 40, 62, and 118 passes were 4.4, 1.0, and 0.1 mW, from which the surface reflectivity was calculated as 94%, 94%, and 95%, respectively. The measured surface reflectivity was less than the theoretical value (99%) of bare gold at midinfrared wavelengths. This discrepancy results from the surface roughness that contributed to light scattering and reduced the output light intensity. Additionally, the experimental depth of focus of the input Gaussian laser beam in the horizontal direction (21 mm) was not much smaller than the cavity radius (25.4 mm) due to the availability of the focusing lens 310, thus the input beam was not yet well approximated by a spherical wave and the beam wavefront did not match perfectly with the cavity surface 10, resulting in some additional beam divergence. Consequently, the light may have been clipped as the beam was coupled out of the cavity 100 after a number of reflections. Furthermore, despite the small output beam size and careful alignment, the output light may not have been fully collected through the OAP 320 to the detector 330, leading again to an apparent reduced surface reflectivity. All these effects are only practical limitations that could be overcome by more refined manufacturing technologies.

The chaotic cavity model was also experimentally validated by testing the prototype copper cavity 100 ($R_0=2.54$ cm, $\epsilon_{x,y}=0.01$, and $\epsilon_{y,z}=0.02$) with a red diode laser. Again, in order to characterize the optical path length in the cavity 100, a pulse-delay experiment was performed by measuring the time delay between a laser pulse coupled into and out of the cavity 100. The setup is illustrated schematically in FIG. 8(b). An AlGaInP diode laser 400 emitting at 661 nm was employed as the source. A pulse generator 450 supplied the diode drive current, which was measured by a wideband current probe. The laser 400 was operated in pulsed mode with a pulse width of 55 μs and a repetition rate of 2.48 kHz, resulting in a peak output power of around 350 mW. The strongly diverging laser beam was collected and focused into the chaotic multi-pass cell 100 through two pairs of spherical lenses 410 having focal lengths of $L_1=25$ mm, $L_2=125$ mm, $L_3=25$ mm, and $L_4=250$ mm. This telescoping lens arrangement significantly reduced the beam size such that light passed through the optical port 30 in the cavity 100. The cavity 100 was again mounted on a rotation stage on top of an x-y-z translation stage to allow light to be injected into the cavity 100 in any specific direction. An OAP mirror 420 focused light coupled out of the cavity 100 onto a high-speed Si detector 430, with a rise time of 20 ns. The amplitude and temporal profile of the detector signal were recorded by a digital oscilloscope 440.

Various multi-passes were achieved by first computing spot patterns and optical path lengths and then setting the corresponding θ and φ values in the setup. Due to the solidly enclosed cavity structure, the spot pattern could not be directly observed in the experiment. Thus, the desired optical path length instead of the beam pattern is again presented and compared with the theoretical prediction.

In order to measure the path length in the cavity 100, the cavity 100 was first oriented at the given θ and φ, and then the temporal envelope and intensity of the pulse coupled out of the cavity 100 was detected. Next, the cavity 100 was slightly moved and the optical port 30 offset from the input beam. The input pulse was reflected from the outer surface of the cell without entering the cavity 100. The reflected beam was subsequently focused by the same parabolic mirror 420, attenuated by a polarizer, and detected by the same detector 430. The polarizer was used to avoid detector saturation. By measuring the time delay between the pulse coupled out of the cavity 100 and the pulse reflected from the cavity surface 10, the optical path length at the specified input beam direction was calculated. Conversely, one could adjust the cavity 100 to some desired optical path length, and then calculate the spot pattern and the corresponding path length from the experimentally identified θ and φ values.

Figure 9A:
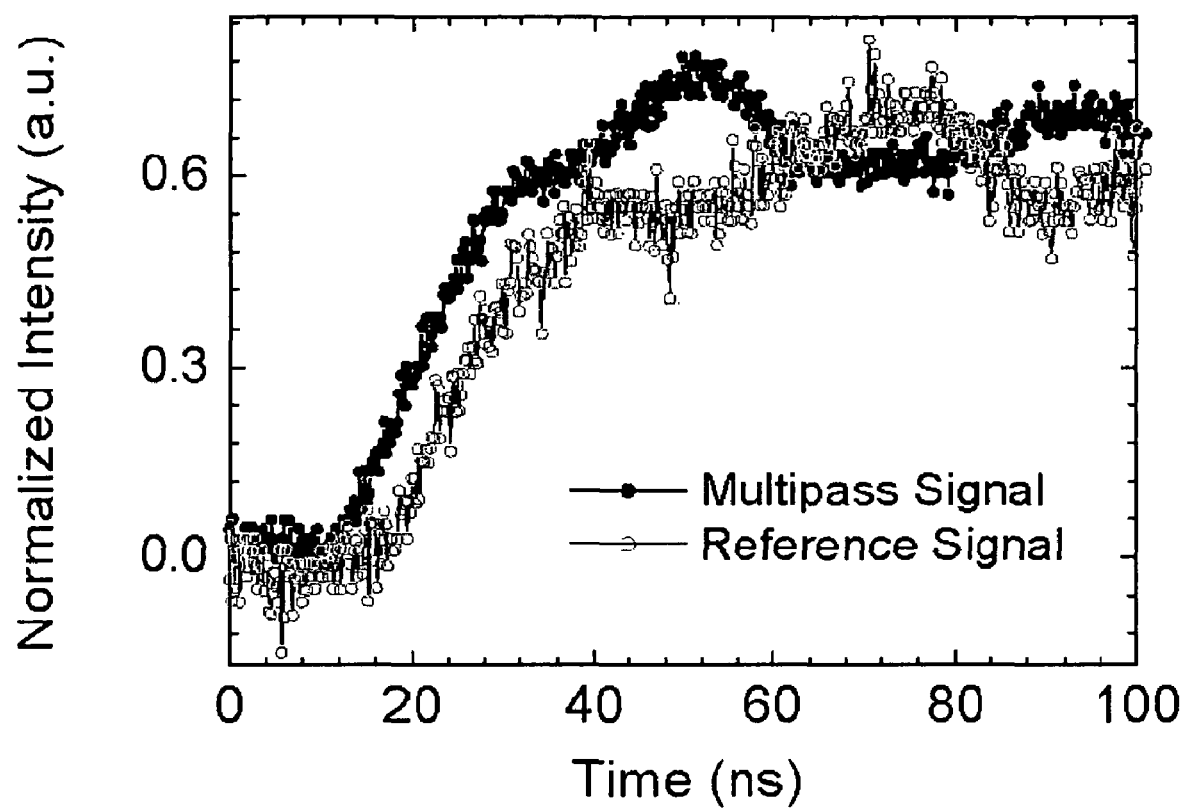
FIG. 9(a) illustrates the measured out-coupled multi-pass light pulse (gray) and the directly reflected pulse (black)
Figure 9B:
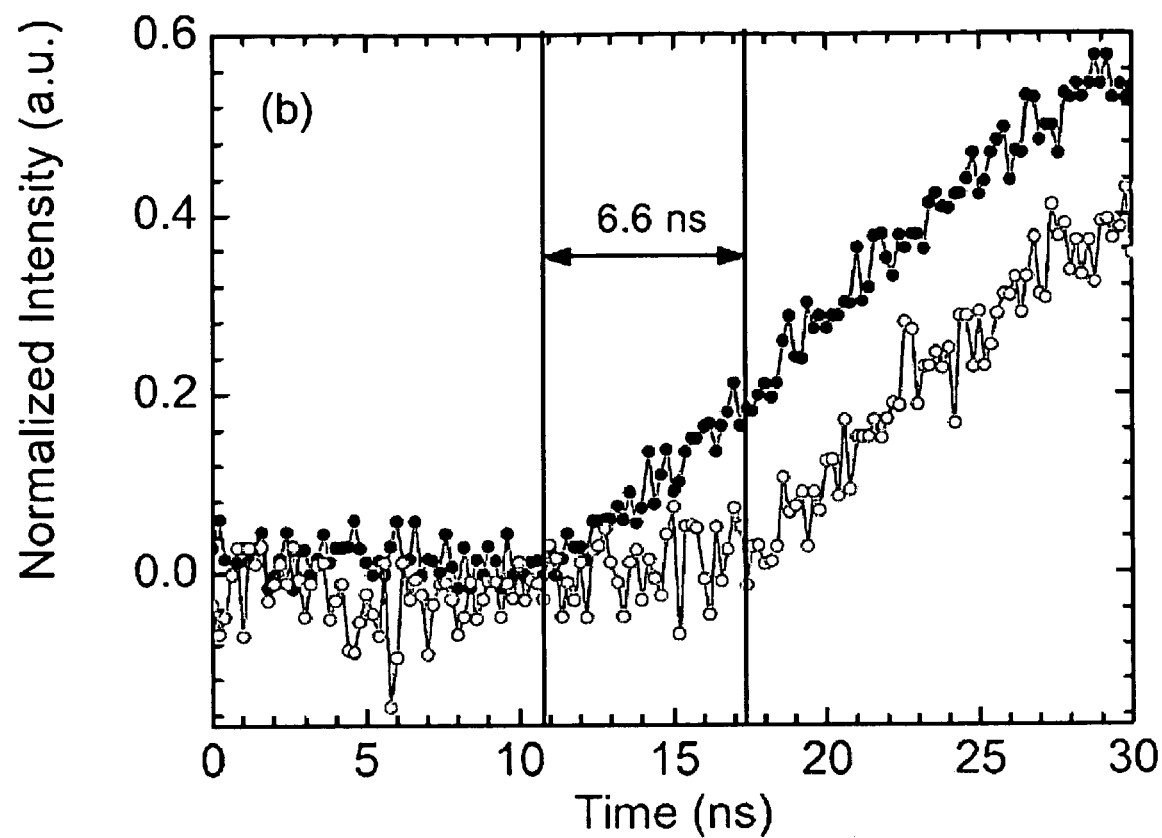
FIG. 9(b) illustrates an enlarged view of FIG. 9(a) showing the time delay between the two pulses in FIG. 9(a)

A very close match was achieved between the observed and calculated initial conditions, and the pulse delay time for various patterns. In this experiment, after setting the cavity 100 to $q_0=(-87°, 5.5°)$ corresponding to the input beam direction of the 40-pass trajectory, FIG. 4(c), a 6.6 ns time delay was measured between the multi-pass and the directly reflected pulse. The 6.6 ns pulse delay corresponds to a ~2 meter path length. FIG. 9 shows the pulse edge data where the pulse coupled from inside the cavity 100 is plotted in gray and the pulse reflected from the outer cavity surface 10 is in black. The pulses are normalized to each other, as illustrated in FIG. 9(a). A close-up of the pulse rising edge is shown in FIG. 9(b). This experimental result agrees well with the theoretical calculation, confirming the predicted ray dynamics and the ability of the chaotic multi-pass cavity 100 to support meter-scale path lengths.

According to the measured intensity of the output beam from the cavity 100, the reflectivity of the gold-coated surface at 661 nm was approximately 0.83. Again, this rather low reflectivity was mainly caused by the scattering effects and the surface roughness. A much higher reflectivity could potentially be achieved by use of ultra-high-reflectivity interference coating or by using longer wavelength laser sources.

Figure 8B:
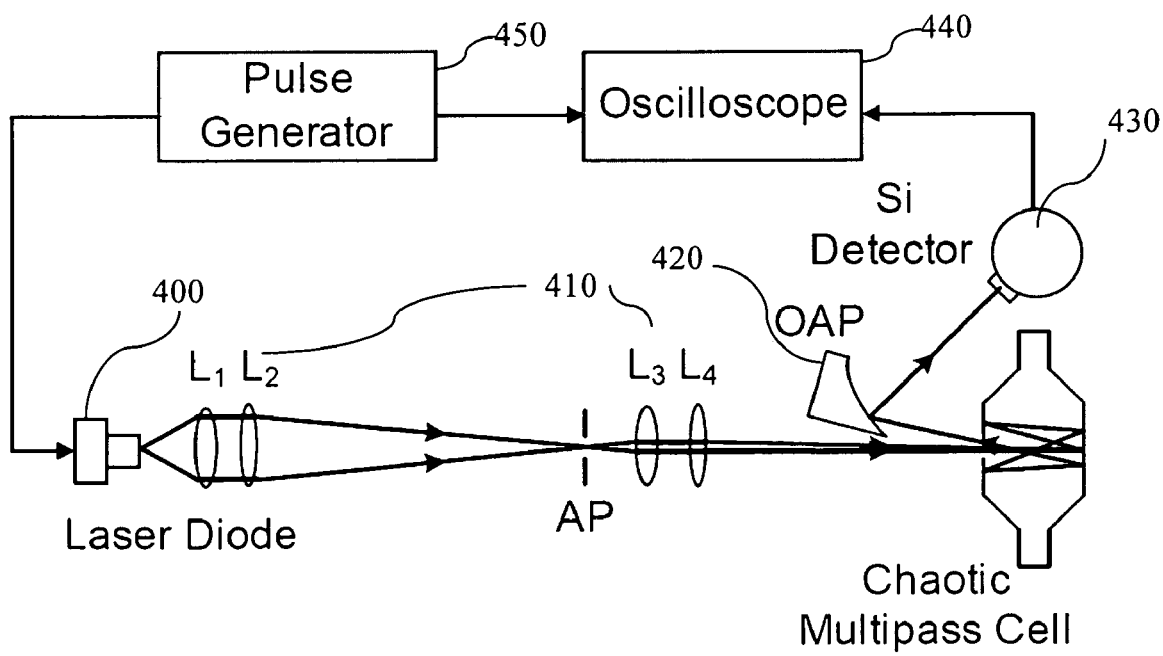

The chaotic multi-pass cavity 100 of the present invention is also ideally suited for inclusion in an optical gas sensing system which may take a form similar to the configuration of the testing systems shown in FIGS. 8(a) and 8(b). For instance, in optical gas sensing system in accordance with the present invention may include a source of electromagnetic radiation, such as a laser 300, 400 which may be provided in the form of a wavelength tunable laser. In addition, a rotationally asymmetric chaotic optical multi-pass cavity 100 in accordance with the present invention may be provided for receiving a gas to be tested through a gas inlet port 42 and for receiving incident electromagnetic radiation from the laser 300, 400 through the optical inlet port 30. Upon making multiple transits through the cavity, the electromagnetic radiation may be emitted from the cavity through the optical inlet port 30 to be received by a detector 330, 430. The detected radiation may then be analyzed to determine the absorption of the incident electromagnetic radiation by the gas as a function of wavelength, thereby providing an indication as to the nature of the gas tested. Unlike the pulse detection systems illustrated in FIGS. 8(*a*) and 8(*b*), a gas sensing system in accordance with the present invention need not include the pulse generator or oscilloscope.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. A rotationally asymmetric chaotic optical multi-pass cavity, comprising a closed reflecting surface that is deformed in two orthogonal directions and includes an optical inlet port for coupling light into the cavity.

2. The rotationally asymmetric chaotic optical multi-pass cavity according to claim 1, wherein the reflecting surface has the shape of a quadrupole in the x-y and the y-z planes.

3. The rotationally asymmetric chaotic optical multi-pass cavity according to claim 1, wherein the optical inlet port is configured to also function as an optical outlet port for coupling light out of the cavity.

4. The rotationally asymmetric chaotic optical multi-pass cavity according to claim 3, comprising an optical outlet port for coupling light out of the cavity.

5. The rotationally asymmetric chaotic optical multi-pass cavity according to claim 1, wherein the shape of the reflecting surface is given by $$x = \frac{R_0[1 + \epsilon_{yz}\cos(2\varphi')]\sin\varphi'[1 + \epsilon_{xy}\cos(2\theta)]\cos(\theta)}{1 - \epsilon_{xy}},$$

$$y = \frac{R_0[1 + \epsilon_{yz}\cos(2\varphi')]\sin\varphi'[1 + \epsilon_{xy}\cos(2\theta)]\sin(\theta)}{1 - \epsilon_{xy}},$$

$$z = R_0[1 + \epsilon_{yz}\cos(2\varphi')]\cos\varphi',$$

where $$\varphi' = \tan^{-1}\left[\frac{(1 - \epsilon_{xy})\cot\varphi}{1 + \epsilon_{xy}\cos(2\theta)}\right],$$

$R_0$ is the mean cavity radius, and $\epsilon_{xy}$ and $\epsilon_{yz}$ are the deformation parameters.

6. The rotationally asymmetric chaotic optical multi-pass cavity according to claim 5, wherein both $\epsilon_{xy}$ and $\epsilon_{yz}$ are non-zero.

7. The rotationally asymmetric chaotic optical multi-pass cavity according to claim 5, wherein $\epsilon_{xy}$ and $\epsilon_{yz}$ have a magnitude sufficient to support quasi-chaotic ray dynamics.

8. The rotationally asymmetric chaotic optical multi-pass cavity according to claim 5, wherein $\epsilon_{xy}$ is about 0.01 and $\epsilon_{yz}$ is about 0.02.

9. The rotationally asymmetric chaotic optical multi-pass cavity according to claim 1, wherein the cavity comprises a first cavity half and a second cavity half each having a reflecting surface, the first and second halves being conjoined to provide the single reflecting surface.

* * * * *